United States Patent
Marliere

(10) Patent No.: US 10,920,253 B2
(45) Date of Patent: Feb. 16, 2021

(54) ENZYMATIC PRODUCTION OF ACETYL PHOSPHATE FROM FORMALDEHYDE

(71) Applicant: SCIENTIST OF FORTUNE S.A., Luxembourg (LU)

(72) Inventor: Philippe Marliere, Tournai (BE)

(73) Assignee: Scientist of Fortune, S.A., Luxembourg (LU)

( * ) Notice: Subject to any disclaimer, the term of this patent is extended or adjusted under 35 U.S.C. 154(b) by 0 days.

(21) Appl. No.: 15/128,530

(22) PCT Filed: Mar. 13, 2015

(86) PCT No.: PCT/EP2015/055254
§ 371 (c)(1),
(2) Date: Sep. 23, 2016

(87) PCT Pub. No.: WO2015/144447
PCT Pub. Date: Oct. 1, 2015

(65) Prior Publication Data
US 2017/0107546 A1    Apr. 20, 2017

(30) Foreign Application Priority Data

Mar. 26, 2014  (EP) .................................... 14161723
Jul. 14, 2014   (EP) .................................... 14176885

(51) Int. Cl.
*C12P 9/00*    (2006.01)

(52) U.S. Cl.
CPC ......... *C12P 9/00* (2013.01); *C12Y 203/03015* (2013.01); *C12Y 401/02009* (2013.01); *C12Y 401/02022* (2013.01)

(58) Field of Classification Search
CPC ....................................................... C12P 9/00
USPC ....................................................... 435/194
See application file for complete search history.

(56) References Cited

U.S. PATENT DOCUMENTS 7,253,001 B2    8/2007  Wahlbom et al.
2012/0222148 A1  8/2012  Turano et al.

FOREIGN PATENT DOCUMENTS

WO        2006016705 A1    2/2006

OTHER PUBLICATIONS

Mitsui et al, Formaldehyde-limited cultivation of a newly isolated methylotrophic bacterium, *Methylobacterium* sp. MF1: enzymatic analysis related to C1 metabolism. J Biosci Bioeng. Jan. 2005;99(1):18-22.*
Rozova et al, Acetate kinase—an enzyme of the postulated phosphoketolase pathway in Methylomicrobium alcaliphilum 20Z. Antonie Van Leeuwenhoek. Oct. 2015;108(4):965-74.*
Sunna et al, Xylanolytic Enzymes from Fungi and Bacteria. Critical Reviews in Biotechnology, 17( 1):39-67 (1997).*
Ruff et al, Sulphoacetaldehyde acetyltransferase yields acetyl phosphate : purification from Alcaligenes defragrans and gene clusters in taurine degradation. Biochem. J. (2003) 369, 275-285.*
Lipmann et al, the Detection of Activated Carboxyl Groups With Hydroxylamine as Interceptor. J. Biol. Chem. 1945, 161:415-416.*
Brenda acylphosphatase (EC 3.6.1.7). Downloaded Sep. 28, 2018.*
Schellenberger et al, Thiamine Pyrophosphate—Carrier of the Catalytic Function of C—C-Splitting Enzymes. Biochemical Education 13(4) 1985 p. 160-163.*
Suzuki et al, Crystal Structures of Phosphoketolase. Journal of Biological Chemistry vol. 285, No. 44, pp. 34279-34287, Oct. 29, 2010.*
Bogorad et al, Building carbon-carbon bonds using a biocatalytic methanol condensation cycle. Proc Natl Acad Sci U S A. Nov. 11, 2014;111(45):15928-33. doi: 10.1073/pnas.1413470111. Epub Oct. 29, 2014.*
Wakayama et al, Regulation of intracellular formaldehyde toxicity during methanol metabolism of the methylotrophic yeast *Pichia methanolica*. J Biosci Bioeng. Nov. 2016;122(5):545-549.*
Grafstron et al, Formaldehyde damage to DNA and inhibition of DNA repair in human bron-chial cells. Science, 220, 216e218 (1983).J Biosci Bioeng. Nov. 2016;122(5):545-549.*
Ke et al, In vitro study on cytotoxicity and intracellular formaldehyde concentration changes after exposure to formaldehyde and its derivatives. Human and Experimental Toxicology 2014, vol. 33(8) 822-830.*
Nishimura et al, A Constitutive Thiamine Metabolism Mutation, thi80, Causing Reduced Thiamine Pyrophosphokinase Activity in *Saccharomyces cerevisiae*. JoURNAL of Bacteriology, Apr. 1991, p. 2716-2719.*
Wakayama et al, Regulation of intracellular formaldehyde toxicity during methanol metabolism of the methylotrophic yeast *Pichia methanolica*. Journal of Bioscience and Bioengineering vol. 122 No. 5, 545e549, 2016.*
Tani et al, Isolation and Characterization of a Mutant of a Methanol Yeast, *Candida boidinii* S2, with Higher Formaldehyde Productivity. Agric. Biol. Chem., 49 (9), 2699-2706, 1985.*
International Search Report and Written Opinion dated Oct. 6, 2016 received in PCT/EP2015/055254.
Extended European Search Report from corresponding EP 14161723. 3, dated Jul. 10, 2014.
International Search Report and Written Opinion from corresponding PCT/EP2015/055254, dated May 20, 2015.

(Continued)

*Primary Examiner* — Sheridan Swope
(74) *Attorney, Agent, or Firm* — Michele M. Wales Ph.D.; Inhouse Patent Counsel, LLC

(57) ABSTRACT

Described is a method for the enzymatic production of acetyl phosphate from formaldehyde using a phosphoketolase or a sulfoacetaldehyde acetyltransferase.

Figure 2:

23 Claims, 2 Drawing Sheets
Specification includes a Sequence Listing.

(56) References Cited

OTHER PUBLICATIONS

Koopman et al., "C1 Compounds as Auxiliary Substrate for Engineered Pseudomonas Putida S12", Applied Microbialogy and Biotechnology, Springer, Berlin, DE, Mar. 12, 2009, Applied Genetics and Molecular Biotechnology, vol. 83, No. 4, pp. 705-713, XP019705566.

Chinen et al., "Innovative Metabolic Pathway Design for Efficient L-Glutamate Production by Suppressing CO2 Emission", The Society for Biotechnology, Journal of Bioscience and Bioengineering, Elsevier, Amsterdam, NL, vol. 103, No. 3, Mar. 1, 2007, pp. 262-269, XP022028172.

Mitsui et al., "Formaldehyde-Limited Cultivation of a Newly Isolated Methylotrophic Bacterium, *Methylobacterium* sp. MF1: Enzymatic Analysis Related to C1 Metabolism", Journal of Bioscience and Bioengineering, vol. 99, No. 1, pp. 18-22, Jan. 1, 2005, Elsevier, Amsterdam, NL, XP027707125.

Ruff et al., "Sulphoacetaldehyde Acetyltransferase Yields Acetyl Phosphate: Purification from Alcaligenes Defragrans and Gene Clusters in Taurine Degradation", Biochem. J., Jan. 1, 2003, vol. 369, pp. 275-285, Konstanz, Germany, XP055126256.

Yurimoto et al., "Assimilation, Dissimilation, and Detoxification of Formaldehyde, a Central Metabolic Intermediate a Methylotrophic Metabolism", The Chemical Record, vol. 5, No. 6, Jan. 1, 2005, pp. 367-375, Kyoto, Japan, XP055126293.

Bogorad, I. et al. "Synthetic Non-Oxidative Glycolysis Enables Complete Carbon Conservation", Nature, vol. 502, pp. 693-697, XP002743423, See Figures 1-2 and 4, (2013).

Chinese Office Action and translation dated Feb. 2, 2019 received in corresponding CN Application 201580015828.7.

Communication under Rule 71(3) EPC dated May 26, 2020 for application No. 15 712 086.6.

He et al., "An Optimized Methanol Assimilation Pathway Relying on Promiscuous Formaldehyde-Condensing Aldolases in *E. coli*", Metabolic Engineering, vol. 60, pp. 1-13 (2020).

Rohr et al., "Phosphoketolase, a Neglected Enzyme of Microbial Carbohydrate Metabolism", Chimia, vol. 56, pp. 270-273 (2002).

Tani et al., "Isolation and Characterization of a Mutant of a Methanol Yeast, *Candida boidinii* S2, with Higher Formaldehyde Productivity", Agricultural and Biological Chemistry, vol. 49, No. 9, pp. 2699-2706, (1985).

Tani et al., "Production of Catalytic Cells for Formaldehyde Production and Alcohol Oxidase by a Catabolite Repression-Insensitive Mutant of a Methanol Yeast, *Candida boidinii* A5 ", Biotechnology and Bioengineering, vol. 32, pp. 1165-1169, (1988).

\* cited by examiner

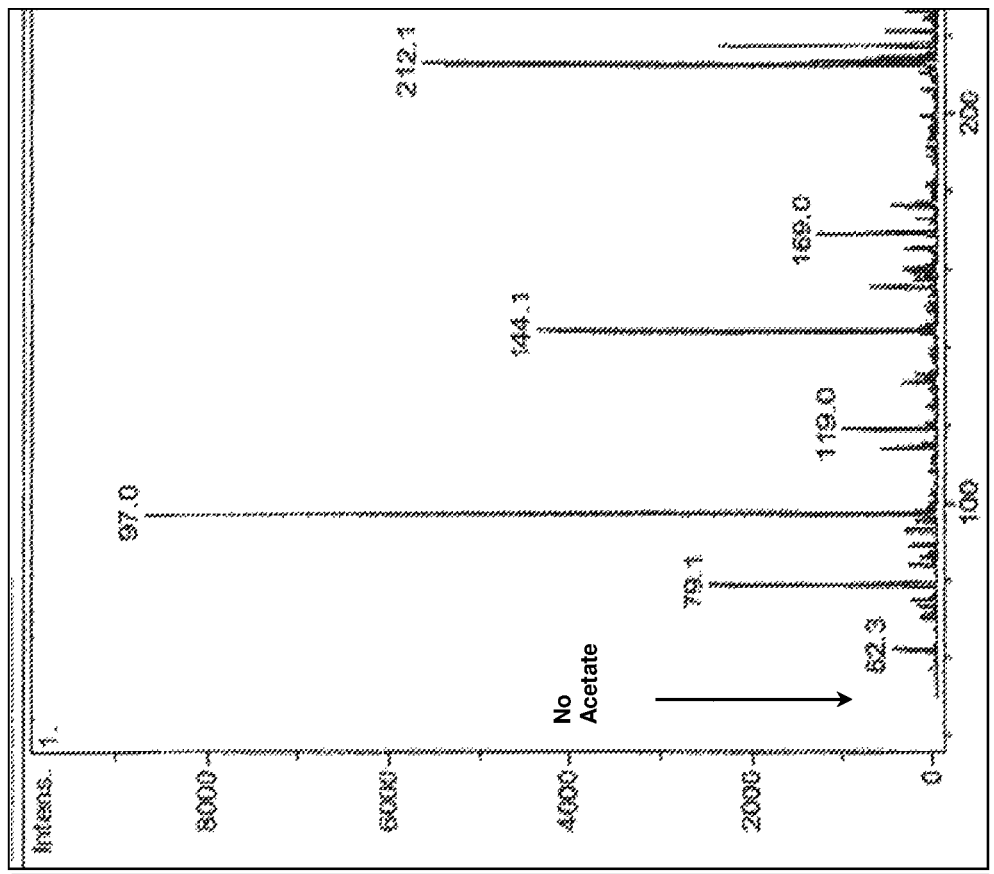
Fig. 1
Fig. 1A
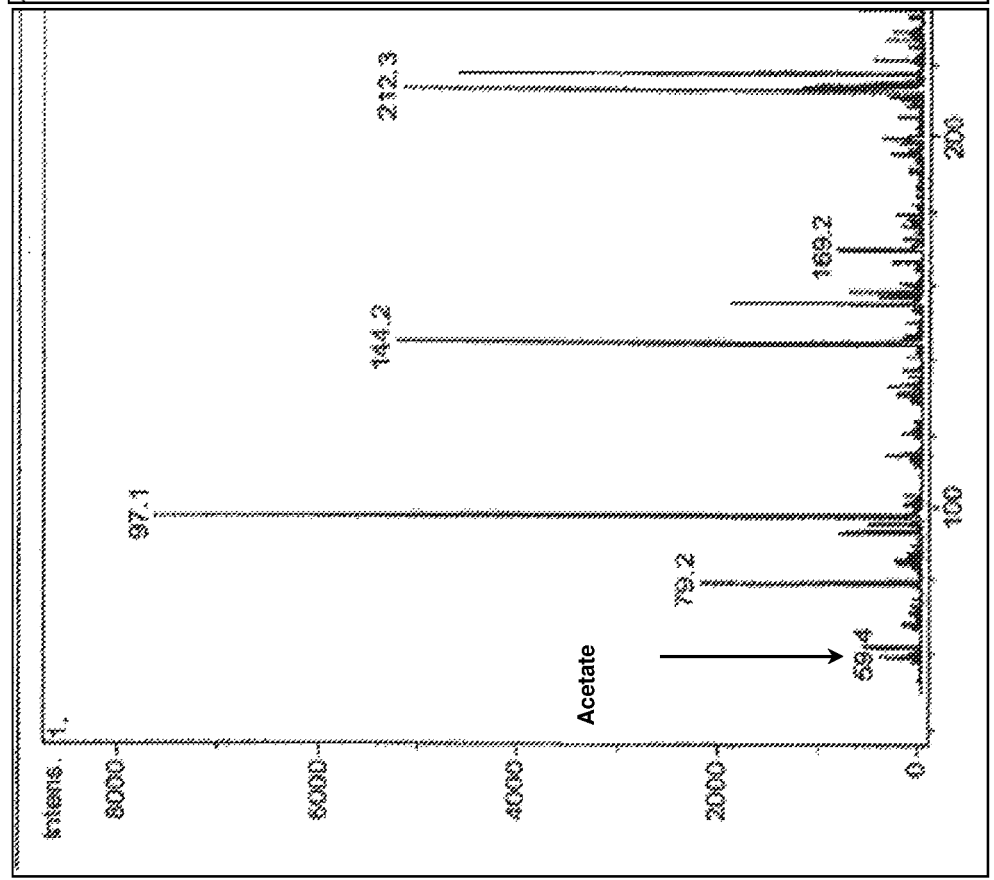
Fig. 1B

```
                        SEQUENCE LISTING

<160> NUMBER OF SEQ ID NOS: 10

<210> SEQ ID NO 1
<211> LENGTH: 825
<212> TYPE: PRT
<213> ORGANISM: Bifidobacterium pseudolongum
<220> FEATURE:
<223> OTHER INFORMATION: subsp. globosum

<400> SEQUENCE: 1

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Thr
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ser Gln Ser Tyr Val Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Met Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320
```

```
Gln Val Pro Leu Ala Ser Ala Arg Asp Thr Glu Glu His Phe Glu Val
            325                 330                 335

Leu Lys Gly Trp Leu Glu Ser Tyr Lys Pro Glu Glu Leu Phe Asn Ala
        340                 345                 350

Asp Gly Ser Ile Lys Asp Val Thr Ala Phe Met Pro Lys Gly Asp
        355                 360                 365

Leu Arg Ile Gly Ala Asn Pro Asn Ala Asn Gly Gly Val Ile Arg Glu
    370                 375                 380

Asp Leu Lys Leu Pro Glu Leu Asp Gln Tyr Glu Val Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Ile
            420                 425                 430

Phe Gly Pro Asp Glu Thr Ala Ser Asn Arg Leu Asn Ala Thr Tyr Glu
        435                 440                 445

Val Thr Asp Lys Gln Trp Asp Asn Gly Tyr Leu Ser Ser Leu Val Asp
    450                 455                 460

Glu His Met Ala Val Thr Gly Gln Val Thr Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Ile Asn Lys Thr Phe Asn Asn Asp His Val Thr Asn Ile Tyr
                565                 570                 575

Phe Ala Thr Asp Ala Asn Met Leu Leu Ala Ile Ser Glu Lys Cys Phe
            580                 585                 590

Lys Ser Thr Asn Lys Ile Asn Ala Ile Phe Ala Gly Lys Gln Pro Ala
        595                 600                 605

Pro Thr Trp Ile Thr Leu Asp Glu Ala Arg Ala Glu Leu Glu Ala Gly
    610                 615                 620

Ala Ala Glu Trp Lys Trp Ala Ser Asn Ala Glu Asn Asn Asp Glu Val
625                 630                 635                 640

Gln Val Val Leu Ala Ala Gly Asp Val Pro Thr Gln Glu Ile Met
                645                 650                 655

Ala Ala Ser Asp Ala Leu Asn Lys Met Gly Ile Lys Phe Lys Val Val
            660                 665                 670

Asn Val Val Asp Leu Leu Lys Leu Gln Ser Arg Glu Asn Asn Asp Glu
        675                 680                 685

Ala Leu Thr Asp Glu Glu Phe Thr Asp Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Asn Val Val Gly Tyr Lys Glu
                725                 730                 735

Gln Gly Ser Thr Thr Thr Pro Phe Asp Met Val Arg Val Asn Asp Met
```

```
            740                 745                 750
Asp Arg Tyr Ala Leu Gln Ala Ala Leu Lys Met Ile Asp Ala Asp
        755                 760                 765

Lys Tyr Ala Asp Lys Ile Asp Glu Leu Asn Ala Phe Arg Gln Lys Ala
        770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Ala Thr Ala Gly Asp Asn Glu
            820                 825

<210> SEQ ID NO 2
<211> LENGTH: 796
<212> TYPE: PRT
<213> ORGANISM: Clostridium acetobutylicum

<400> SEQUENCE: 2

Met Gln Ser Ile Ile Gly Lys His Lys Asp Glu Gly Lys Ile Thr Pro
1               5                   10                  15

Glu Tyr Leu Lys Lys Ile Asp Ala Tyr Trp Arg Ala Ala Asn Phe Ile
            20                  25                  30

Ser Val Gly Gln Leu Tyr Leu Leu Asp Asn Pro Leu Leu Arg Glu Pro
        35                  40                  45

Leu Lys Pro Glu His Leu Lys Arg Lys Val Val Gly His Trp Gly Thr
    50                  55                  60

Ile Pro Gly Gln Asn Phe Ile Tyr Ala His Leu Asn Arg Val Ile Lys
65                  70                  75                  80

Lys Tyr Asp Leu Asp Met Ile Tyr Val Ser Gly Pro Gly His Gly Gly
                85                  90                  95

Gln Val Met Val Ser Asn Ser Tyr Leu Asp Gly Thr Tyr Ser Glu Val
            100                 105                 110

Tyr Pro Asn Val Ser Arg Asp Leu Asn Gly Leu Lys Lys Leu Cys Lys
        115                 120                 125

Gln Phe Ser Phe Pro Gly Gly Ile Ser Ser His Met Ala Pro Glu Thr
    130                 135                 140

Pro Gly Ser Ile Asn Glu Gly Gly Glu Leu Gly Tyr Ser Leu Ala His
145                 150                 155                 160

Ser Phe Gly Ala Val Phe Asp Asn Pro Asp Leu Ile Thr Ala Cys Val
                165                 170                 175

Val Gly Asp Gly Glu Ala Glu Thr Gly Pro Leu Ala Thr Ser Trp Gln
            180                 185                 190

Ala Asn Lys Phe Leu Asn Pro Val Thr Asp Gly Ala Val Leu Pro Ile
        195                 200                 205

Leu His Leu Asn Gly Tyr Lys Ile Ser Asn Pro Thr Val Leu Ser Arg
    210                 215                 220

Ile Pro Lys Asp Glu Leu Glu Lys Phe Phe Glu Gly Asn Gly Trp Lys
225                 230                 235                 240

Pro Tyr Phe Val Glu Gly Glu Asp Pro Glu Thr Met His Lys Leu Met
                245                 250                 255

Ala Glu Thr Leu Asp Ile Val Thr Glu Glu Ile Leu Asn Ile Gln Lys
            260                 265                 270

Asn Ala Arg Glu Asn Asn Asp Cys Ser Arg Pro Lys Trp Pro Met Ile
        275                 280                 285
```

```
Val Leu Arg Thr Pro Lys Gly Trp Thr Gly Pro Lys Phe Val Asp Gly
290                 295                 300

Val Pro Asn Glu Gly Ser Phe Arg Ala His Gln Val Pro Leu Ala Val
305                 310                 315                 320

Asp Arg Tyr His Thr Glu Asn Leu Asp Gln Leu Glu Glu Trp Leu Lys
                325                 330                 335

Ser Tyr Lys Pro Glu Glu Leu Phe Asp Glu Asn Tyr Arg Leu Ile Pro
            340                 345                 350

Glu Leu Glu Glu Leu Thr Pro Lys Gly Asn Lys Arg Met Ala Ala Asn
        355                 360                 365

Leu His Ala Asn Gly Gly Leu Leu Leu Arg Glu Leu Arg Thr Pro Asp
    370                 375                 380

Phe Arg Asp Tyr Ala Val Asp Val Pro Thr Pro Gly Ser Thr Val Lys
385                 390                 395                 400

Gln Asp Met Ile Glu Leu Gly Lys Tyr Val Arg Asp Val Val Lys Leu
                405                 410                 415

Asn Glu Asp Thr Arg Asn Phe Arg Ile Phe Gly Pro Asp Glu Thr Met
                420                 425                 430

Ser Asn Arg Leu Trp Ala Val Phe Glu Gly Thr Lys Arg Gln Trp Leu
        435                 440                 445

Ser Glu Ile Lys Glu Pro Asn Asp Glu Phe Leu Ser Asn Asp Gly Arg
    450                 455                 460

Ile Val Asp Ser Met Leu Ser Glu His Leu Cys Glu Gly Trp Leu Glu
465                 470                 475                 480

Gly Tyr Leu Leu Thr Gly Arg His Gly Phe Phe Ala Ser Tyr Glu Ala
                485                 490                 495

Phe Leu Arg Ile Val Asp Ser Met Ile Thr Gln His Gly Lys Trp Leu
                500                 505                 510

Lys Val Thr Ser Gln Leu Pro Trp Arg Lys Asp Ile Ala Ser Leu Asn
        515                 520                 525

Leu Ile Ala Thr Ser Asn Val Trp Gln Gln Asp His Asn Gly Tyr Thr
    530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
                565                 570                 575

Phe Asp Lys Cys Leu His Thr Lys His Lys Ile Asn Leu Leu Val Thr
                580                 585                 590

Ser Lys His Pro Arg Gln Gln Trp Leu Thr Met Asp Gln Ala Val Lys
        595                 600                 605

His Val Glu Gln Gly Ile Ser Ile Trp Asp Trp Ala Ser Asn Asp Lys
    610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                645                 650                 655

Leu Lys Val Arg Phe Val Asn Val Val Asp Met Met Lys Leu Leu Pro
                660                 665                 670

Glu Asn Glu His Pro His Gly Leu Ser Asp Lys Asp Tyr Asn Ala Leu
        675                 680                 685

Phe Thr Thr Asp Lys Pro Val Ile Phe Ala Phe His Gly Phe Ala His
    690                 695                 700

Leu Ile Asn Gln Leu Thr Tyr His Arg Glu Asn Arg Asn Leu His Val
```

```
                  705                 710                 715                 720
His Gly Tyr Met Glu Glu Gly Thr Ile Thr Thr Pro Phe Asp Met Arg
                    725                 730                 735

Val Gln Asn Lys Leu Asp Arg Phe Asn Leu Val Lys Asp Val Val Glu
                    740                 745                 750

Asn Leu Pro Gln Leu Gly Asn Arg Gly Ala His Leu Val Gln Leu Met
                    755                 760                 765

Asn Asp Lys Leu Val Glu His Asn Gln Tyr Ile Arg Glu Val Gly Glu
                    770                 775                 780

Asp Leu Pro Glu Ile Thr Asn Trp Gln Trp His Val
785                 790                 795

<210> SEQ ID NO 3
<211> LENGTH: 822
<212> TYPE: PRT
<213> ORGANISM: Lactococcus lactis
<220> FEATURE:
<223> OTHER INFORMATION: subsp. lactis

<400> SEQUENCE: 3

Met Thr Glu Tyr Asn Ser Glu Ala Tyr Leu Lys Lys Leu Asp Lys Trp
1               5                   10                  15

Trp Arg Ala Ala Thr Tyr Leu Gly Ala Gly Met Ile Phe Leu Lys Glu
                20                  25                  30

Asn Pro Leu Phe Ser Val Thr Gly Thr Pro Ile Lys Ala Glu Asn Leu
            35                  40                  45

Lys Ala Asn Pro Ile Gly His Trp Gly Thr Val Ser Gly Gln Thr Phe
        50                  55                  60

Leu Tyr Ala His Ala Asn Arg Leu Ile Asn Lys Tyr Asn Gln Lys Met
65                  70                  75                  80

Phe Tyr Met Gly Gly Pro Gly His Gly Gln Ala Met Val Val Pro
                85                  90                  95

Ser Tyr Leu Asp Gly Ser Tyr Thr Glu Ala Tyr Pro Glu Ile Thr Gln
                100                 105                 110

Asp Leu Glu Gly Met Ser Arg Leu Phe Lys Arg Phe Ser Phe Pro Gly
            115                 120                 125

Gly Ile Gly Ser His Met Thr Ala Gln Thr Pro Gly Ser Leu His Glu
        130                 135                 140

Gly Gly Glu Leu Gly Tyr Val Leu Ser His Ala Thr Gly Ala Ile Leu
145                 150                 155                 160

Asp Gln Pro Glu Gln Ile Ala Phe Ala Val Val Gly Asp Gly Glu Ala
                165                 170                 175

Glu Thr Gly Pro Leu Met Thr Ser Trp His Ser Ile Lys Phe Ile Asn
                180                 185                 190

Pro Lys Asn Asp Gly Ala Ile Leu Pro Ile Leu Asp Leu Asn Gly Phe
            195                 200                 205

Lys Ile Ser Asn Pro Thr Leu Phe Ala Arg Thr Ser Asp Val Asp Ile
        210                 215                 220

Arg Lys Phe Phe Glu Gly Leu Gly Tyr Ser Pro Arg Tyr Ile Glu Asn
225                 230                 235                 240

Asp Asp Ile His Asp Tyr Met Ala Tyr His Lys Leu Ala Ala Glu Val
                245                 250                 255

Phe Asp Lys Ala Ile Glu Asp Ile His Gln Ile Gln Lys Asp Ala Arg
                260                 265                 270

Glu Asp Asn Arg Tyr Gln Asn Gly Glu Ile Pro Ala Trp Pro Ile Val
```

```
                275                 280                 285
Ile Ala Arg Leu Pro Lys Gly Trp Gly Pro Arg Tyr Asn Asp Trp
    290                 295                 300
Ser Gly Pro Lys Phe Asp Gly Lys Gly Met Pro Ile Glu His Ser Phe
305                 310                 315                 320
Arg Ala His Gln Val Pro Leu Pro Leu Ser Lys Asn Met Gly Thr
                325                 330                 335
Leu Pro Glu Phe Val Lys Trp Met Thr Ser Tyr Gln Pro Glu Thr Leu
                340                 345                 350
Phe Asn Ala Asp Gly Ser Leu Lys Glu Glu Leu Arg Asp Phe Ala Pro
                355                 360                 365
Lys Gly Glu Met Arg Met Ala Ser Asn Pro Val Thr Asn Gly Gly Val
    370                 375                 380
Asp Tyr Ser Asn Leu Val Leu Pro Asp Trp Gln Glu Phe Ala Asn Pro
385                 390                 395                 400
Ile Ser Glu Asn Asn Arg Gly Lys Leu Leu Pro Asp Thr Asn Asp Asn
                405                 410                 415
Met Asp Met Asn Val Leu Ser Lys Tyr Phe Ala Glu Ile Val Lys Leu
                420                 425                 430
Asn Pro Thr Arg Phe Arg Leu Phe Gly Pro Asp Glu Thr Met Ser Asn
                435                 440                 445
Arg Phe Trp Glu Met Phe Lys Val Thr Asn Arg Gln Trp Met Gln Val
    450                 455                 460
Ile Lys Asn Pro Asn Asp Glu Phe Ile Ser Pro Glu Gly Arg Ile Ile
465                 470                 475                 480
Asp Ser Gln Leu Ser Glu His Gln Ala Glu Gly Trp Leu Glu Gly Tyr
                485                 490                 495
Thr Leu Thr Gly Arg Thr Gly Val Phe Ala Ser Tyr Glu Ser Phe Leu
                500                 505                 510
Arg Val Val Asp Ser Met Leu Thr Gln His Phe Lys Trp Ile Arg Gln
                515                 520                 525
Ala Ala Asp Gln Lys Trp Arg His Asp Tyr Pro Ser Leu Asn Val Ile
    530                 535                 540
Ser Thr Ser Thr Val Phe Gln Gln Asp His Asn Gly Tyr Thr His Gln
545                 550                 555                 560
Asp Pro Gly Met Leu Thr His Leu Ala Glu Lys Lys Ser Asp Phe Ile
                565                 570                 575
Arg Gln Tyr Leu Pro Ala Asp Gly Asn Thr Leu Leu Ala Val Phe Asp
                580                 585                 590
Arg Ala Phe Gln Asp Arg Ser Lys Ile Asn His Ile Val Ala Ser Lys
    595                 600                 605
Gln Pro Arg Gln Gln Trp Phe Thr Lys Glu Glu Ala Glu Lys Leu Ala
    610                 615                 620
Thr Asp Gly Ile Ala Thr Ile Asp Trp Ala Ser Thr Ala Lys Asp Gly
625                 630                 635                 640
Glu Ala Val Asp Leu Val Phe Ala Ser Ala Gly Ala Glu Pro Thr Ile
                645                 650                 655
Glu Thr Leu Ala Ala Leu His Leu Val Asn Glu Val Phe Pro Gln Ala
                660                 665                 670
Lys Phe Arg Tyr Val Asn Val Val Glu Leu Gly Arg Leu Gln Lys Lys
    675                 680                 685
Lys Gly Ala Leu Asn Gln Glu Arg Glu Leu Ser Asp Glu Glu Phe Glu
    690                 695                 700
```

```
Lys Tyr Phe Gly Pro Ser Gly Thr Pro Val Ile Phe Gly Phe His Gly
705                 710                 715                 720

Tyr Glu Asp Leu Ile Glu Ser Ile Phe Tyr Gln Arg Gly His Asp Gly
            725                 730                 735

Leu Ile Val His Gly Tyr Arg Glu Asp Gly Asp Ile Thr Thr Thr Tyr
        740                 745                 750

Asp Met Arg Val Tyr Ser Glu Leu Asp Arg Phe His Gln Ala Ile Asp
    755                 760                 765

Ala Met Gln Val Leu Tyr Val Asn Arg Lys Val Asn Gln Gly Leu Ala
770                 775                 780

Lys Ala Phe Ile Asp Arg Met Glu Arg Thr Leu Val Lys His Phe Glu
785                 790                 795                 800

Val Thr Arg Asn Glu Gly Val Asp Ile Pro Glu Phe Thr Glu Trp Val
                805                 810                 815

Trp Ser Asp Leu Lys Lys
            820

<210> SEQ ID NO 4
<211> LENGTH: 598
<212> TYPE: PRT
<213> ORGANISM: Castellaniella defragrans

<400> SEQUENCE: 4

Met Ala Asn Asp Thr Arg Gln Val Val Gln Gly Val Gln Glu Met Thr
1               5                   10                  15

Pro Ser Glu Ala Phe Val Glu Thr Met Val Ala Asn Gly Val Thr Glu
            20                  25                  30

Ile Phe Gly Ile Met Gly Ser Ala Phe Met Asp Ala Met Asp Ile Phe
        35                  40                  45

Ala Pro Ala Gly Ile Lys Leu Ile Pro Val Val His Glu Gln Gly Ala
50                  55                  60

Ala His Met Ala Asp Gly Phe Ala Arg Val Ser Gly Arg Thr Gly Val
65                  70                  75                  80

Val Ile Gly Gln Asn Gly Pro Gly Ile Ser Asn Cys Val Thr Ala Ile
                85                  90                  95

Ala Ala Ala Tyr Trp Ala His Thr Pro Val Val Ile Val Thr Pro Glu
            100                 105                 110

Ala Gly Thr Thr Gly Ile Gly Leu Gly Gly Phe Gln Glu Ala Arg Gln
        115                 120                 125

Leu Pro Met Phe Gln Glu Phe Thr Lys Tyr Gln Gly His Val Thr His
    130                 135                 140

Pro Ala Arg Met Ala Glu Tyr Thr Ala Arg Cys Phe Ala Arg Ala Arg
145                 150                 155                 160

Asp Glu Met Gly Pro Ala Gln Leu Asn Ile Pro Arg Asp Tyr Phe Tyr
                165                 170                 175

Gly Lys Ile Lys Cys Glu Ile Pro Leu Pro Gln Pro Leu Asp Arg Gly
            180                 185                 190

Pro Gly Gly Ala Gln Ser Leu Asp Ala Ala Arg Leu Leu Ala Glu
        195                 200                 205

Ala Lys Phe Pro Val Ile Ile Ser Gly Gly Val Val Met Gly Asp
    210                 215                 220

Ala Val Glu Glu Cys Lys Ala Leu Ala Glu Arg Leu Gly Ala Pro Val
225                 230                 235                 240

Val Asn Ser Tyr Leu His Asn Asp Ser Phe Pro Ala Ser His Pro Leu
```

-continued

```
                245                 250                 255

Trp Cys Gly Pro Leu Gly Tyr Gln Gly Ser Lys Ala Ala Met Lys Leu
            260                 265                 270

Leu Ala Asp Ala Asp Val Val Leu Ala Leu Gly Thr Arg Leu Gly Pro
        275                 280                 285

Phe Gly Thr Leu Pro Gln His Gly Leu Asp Tyr Trp Pro Lys Asn Ala
    290                 295                 300

Arg Ile Ile Gln Val Asp Ala Asp Ser Lys Met Leu Gly Leu Val Lys
305                 310                 315                 320

Lys Ile Thr Val Gly Val Cys Gly Asp Ala Lys Ala Ser Ala Ala Glu
                325                 330                 335

Ile Ser Arg Arg Ile Asp Gly Met Lys Leu Ala Cys Asp Ala Asn Lys
            340                 345                 350

Ala Glu Arg Ala Ala Arg Ile Gln Ala Glu Lys Asp Ala Trp Glu Gln
        355                 360                 365

Glu Leu Thr Asp Trp Thr His Glu Arg Asp Pro Phe Ser Leu Asp Met
    370                 375                 380

Ile Glu Glu Gln Ser Lys Glu Glu Gly Asn Trp Leu His Pro Arg Gln
385                 390                 395                 400

Val Leu Arg Glu Leu Glu Lys Ala Met Pro Glu Asp Val Met Val Ser
                405                 410                 415

Thr Asp Ile Gly Asn Ile Asn Ser Val Ala Asn Ser Tyr Leu Arg Phe
            420                 425                 430

Glu Lys Pro Arg Ser Phe Phe Ala Ala Met Ser Trp Gly Asn Cys Gly
        435                 440                 445

Tyr Ala Phe Pro Thr Ile Ile Gly Ala Lys Val Ala Ala Pro His Arg
    450                 455                 460

Pro Ala Val Ser Tyr Ala Gly Asp Gly Ala Trp Gly Met Ser Met Ser
465                 470                 475                 480

Glu Ile Met Thr Cys Val Arg His Asp Ile Pro Val Thr Ala Val Val
                485                 490                 495

Phe His Asn Arg Gln Trp Gly Ala Glu Lys Lys Asn Gln Val Asp Phe
            500                 505                 510

Tyr Asn Arg Arg Phe Val Ala Gly Glu Leu Glu Ser Glu Ser Phe Ala
        515                 520                 525

Gly Ile Ala Arg Ala Met Gly Ala Glu Gly Val Val Val Asp Arg Ile
    530                 535                 540

Glu Asp Val Gly Pro Ala Leu Lys Lys Ala Ile Asp Ala Gln Met Asn
545                 550                 555                 560

Asp Arg Lys Thr Thr Val Ile Glu Ile Met Cys Thr Arg Glu Leu Gly
                565                 570                 575

Asp Pro Phe Arg Arg Asp Ala Leu Ser Lys Pro Val Arg Leu Leu Glu
            580                 585                 590

Lys Tyr Arg Asp Tyr Thr
        595

<210> SEQ ID NO 5
<211> LENGTH: 603
<212> TYPE: PRT
<213> ORGANISM: Alcaligenes xylosoxydans
<220> FEATURE:
<223> OTHER INFORMATION: subsp. xylosoxydans

<400> SEQUENCE: 5

Met Ala Ala Thr Asp Asn Arg Lys Val Val Glu Gly Val His Lys Met
```

```
1               5                   10                  15
Thr Pro Ser Glu Ala Phe Val Glu Thr Cys Val Ala Asn Gly Val Ser
                20                  25                  30

Glu Met Phe Gly Ile Met Gly Ser Ala Phe Met Asp Ala Met Asp Ile
            35                  40                  45

Phe Ala Pro Ala Gly Ile Arg Leu Ile Pro Val Val His Glu Gln Gly
        50                  55                  60

Ala Ala His Met Ala Asp Gly Tyr Ala Arg Val Ser Gly Arg His Gly
65                  70                  75                  80

Val Val Ile Gly Gln Asn Gly Pro Gly Ile Ser Asn Cys Val Thr Gly
                85                  90                  95

Ile Ala Ala Ala Tyr Trp Ala His Ser Pro Val Val Ile Val Thr Pro
            100                 105                 110

Glu Thr Gly Thr Met Gly Met Gly Leu Gly Gly Phe Gln Glu Ala Asn
        115                 120                 125

Gln Leu Pro Met Phe Gln Glu Phe Thr Lys Tyr Gln Gly His Val Cys
        130                 135                 140

Asn Pro Lys Arg Met Ala Glu Phe Thr Gly Arg Val Phe Asp Arg Ala
145                 150                 155                 160

Met Ser Glu Met Gly Pro Thr Gln Leu Asn Ile Pro Arg Asp Tyr Phe
                165                 170                 175

Tyr Gly Glu Ile Glu Cys Glu Ile Pro Lys Pro Met Arg Val Asp Arg
            180                 185                 190

Gly His Gly Gly Glu Ala Ser Leu Gln Ala Ala Val Glu Leu Leu Lys
        195                 200                 205

Thr Ala Lys Phe Pro Val Ile Leu Ala Gly Gly Val Val Met Gly
        210                 215                 220

Asp Ala Val Glu Glu Ala Lys Gln Leu Ala Glu Arg Leu Gly Ala Pro
225                 230                 235                 240

Val Ala Thr Gly Tyr Leu Arg Asn Asp Ala Phe Pro Ala Lys His Pro
                245                 250                 255

Leu Trp Ala Gly Pro Leu Gly Tyr Gln Gly Ser Lys Ala Ala Met Lys
            260                 265                 270

Leu Ile Ala Gln Ala Asp Val Val Ile Ala Leu Gly Ser Arg Met Gly
        275                 280                 285

Pro Phe Gly Thr Leu Pro Gln His Gly Met Asp Tyr Trp Pro Lys Ala
        290                 295                 300

Ala Lys Ile Ile Gln Ile Glu Ala Asp His Thr Asn Leu Gly Leu Val
305                 310                 315                 320

Lys Lys Ile Ala Val Gly Ile Asn Gly Asp Ala Lys Val Ala Ala
                325                 330                 335

Glu Leu Ser Arg Arg Leu Ala Asp Val Thr Leu Gly Cys Asp Ala Thr
            340                 345                 350

Lys Ala Ala Arg Ala Asp Thr Ile Ala Thr Glu Lys Ala Ala Trp Glu
        355                 360                 365

Lys Glu Leu Asp Gly Trp Thr His Glu Arg Asp Pro Tyr Ser Leu Asp
        370                 375                 380

Met Ile Glu Glu Ala Lys Gly Glu Arg Thr Pro Thr Gly Gly Ser Tyr
385                 390                 395                 400

Leu His Pro Arg Gln Val Leu Arg Glu Leu Glu Lys Ala Met Pro Ala
                405                 410                 415

Arg Val Met Val Ser Thr Asp Ile Gly Asn Ile Asn Ser Val Ala Asn
            420                 425                 430
```

```
Ser Tyr Leu Arg Phe Asp Glu Pro Arg Ser Phe Phe Ala Pro Met Ser
        435                 440                 445

Phe Gly Asn Cys Gly Tyr Ala Leu Pro Thr Ile Ile Gly Ala Lys Cys
    450                 455                 460

Ala Ala Pro Asp Arg Pro Ala Ile Ala Tyr Ala Gly Asp Gly Ala Trp
465                 470                 475                 480

Gly Met Ser Met Met Glu Ile Met Thr Ala Val Arg His Asp Ile Pro
            485                 490                 495

Val Thr Ala Val Val Phe His Asn Arg Gln Trp Gly Ala Glu Lys Lys
            500                 505                 510

Asn Gln Val Asp Phe Tyr Asn Arg Arg Phe Val Ala Gly Glu Leu Glu
            515                 520                 525

Ser Glu Ser Phe Ser Asp Ile Ala Lys Ala Met Gly Ala Glu Gly Ile
    530                 535                 540

Val Val Asp His Ile Glu Asp Val Gly Pro Ala Leu Gln Lys Ala Ile
545                 550                 555                 560

Asp Met Gln Met Lys Glu Gly Lys Thr Cys Val Ile Glu Ile Met Cys
                565                 570                 575

Thr Arg Glu Leu Gly Asp Pro Phe Arg Arg Asp Ala Leu Ser Lys Pro
            580                 585                 590

Val Arg Met Leu Asp Lys Tyr Lys Asp Tyr Val
            595                 600

<210> SEQ ID NO 6
<211> LENGTH: 584
<212> TYPE: PRT
<213> ORGANISM: Desulfonispora thiosulfatigenes

<400> SEQUENCE: 6

Met Ala Lys Val Lys Met Thr Pro Ser Glu Ala Met Thr Glu Val Leu
1               5                   10                  15

Val Asn Glu Gly Val Thr His Val Thr Gly Ile Leu Gly Ser Ala Phe
            20                  25                  30

Met Asp Met Leu Asp Leu Trp Pro Thr Ala Gly Ile Glu Phe Ile Ala
        35                  40                  45

Val Arg His Glu Gln Thr Ala Gly His Met Gln Asp Ala Tyr Cys Arg
    50                  55                  60

Ile Thr Gly Lys Ala Ser Val Cys Ile Gly Gln Asn Gly Pro Gly Val
65                  70                  75                  80

Thr Asn Leu Val Thr Cys Val Ala Ala Ala Asn Gln Ala His Thr Pro
                85                  90                  95

Met Val Val Leu Gly Pro Ser Ala Gly Thr Pro Thr Val Gly Trp Asp
            100                 105                 110

Gly Phe Gln Glu Cys Asp Gln Val Ser Ile Phe Arg Ser Ile Thr Lys
        115                 120                 125

Gln Val Leu Gln Val Pro His Pro Ser Arg Ala Gly Asp Val Leu Arg
    130                 135                 140

Thr Ala Phe Arg Ile Ala Tyr Ala Glu Arg Gly Pro Val Tyr Val Asp
145                 150                 155                 160

Ile Pro Arg Asn Tyr Phe Tyr Gly Glu Val Tyr Glu Glu Ile Leu Arg
                165                 170                 175

Pro Asp Gln Tyr Arg Ala Met Asn Val Arg Gly Ala Gly Asp Ala Thr
            180                 185                 190

Glu Leu Ala Arg Ala Thr Glu Ile Leu Ala Ala Ala Lys Asn Pro Val
```

```
                195                 200                 205
Ile Ile Ser Gly Arg Gly Val Asp Ala Asp Ala Phe Ala Glu Val
            210                 215                 220
Lys Glu Ile Ala His Met Leu Thr Ala Pro Val Ala Met Ser Tyr Leu
225                 230                 235                 240
His Asn Asp Thr Tyr Pro Ala Asp Asp Glu Leu Trp Val Gly Pro Ile
                245                 250                 255
Gly Tyr Met Gly Ala Lys Ser Ala Met Tyr Ser Leu Gln Asp Ala Asp
                260                 265                 270
Val Ile Leu Ala Ile Gly Ser Arg Leu Ser Val Phe Gly Thr Leu Pro
            275                 280                 285
Gln Tyr Asp Ile Asn Tyr Phe Pro Glu Asn Ala Lys Ile Ile Gln Ile
            290                 295                 300
Glu Val Asn Pro Lys Gln Ile Gly Arg Arg His Pro Val Thr Val Pro
305                 310                 315                 320
Ile Ile Gly Asp Ala Lys Leu Ala Thr Ala Glu Leu Ile Lys Leu Leu
                325                 330                 335
Lys Ala Lys Gly Asp Val Lys Pro Asn Ala Glu Arg Leu Ala Lys Ile
            340                 345                 350
Gln Glu Arg Arg Asn Asp Trp Phe Lys Glu Ile Glu Met Ala Met
            355                 360                 365
Met Pro Gly Asn Pro Ile Asn Pro Arg Arg Val Leu Phe Glu Val Ala
370                 375                 380
Lys Leu Met Pro Glu Asp Ala Ile Leu Thr Thr Asp Ile Gly Asn Val
385                 390                 395                 400
Ala Ser Thr Ala Asn Ser Tyr Phe Lys Phe Thr Lys Pro Lys Lys His
                405                 410                 415
Ile Ala Ala Leu Thr Phe Gly Asn Thr Gly Phe Ala Tyr Gln Ala Gly
            420                 425                 430
Leu Gly Ala Gln Met Ala Glu Pro Asp Ser Pro Val Val Ala Ile Val
            435                 440                 445
Gly Asp Gly Ala Trp Gly Gln Ser Leu His Glu Ile Ser Thr Ala Val
            450                 455                 460
Gln Tyr Lys Leu Pro Val Ile Ala Cys Val Phe Arg Asn Met Ala Trp
465                 470                 475                 480
Cys Ala Glu Lys Lys Asn Gln Ile Asp Phe Tyr Asn Asn Arg Phe Val
                485                 490                 495
Gly Thr Glu Ile Pro Asn Pro Ile Ser Phe Ile Pro Ala Ala Glu Ala
                500                 505                 510
Phe Gly Ala Lys Gly Ile Arg Val Glu Lys Pro Glu Asp Ile Ala Asp
            515                 520                 525
Ala Phe Lys Gln Gly Leu Ala Trp Arg Ala Glu Gly His Pro Val Val
            530                 535                 540
Leu Glu Phe Val Val Asp Gly Thr Ile Leu Ala Pro Pro Phe Arg Lys
545                 550                 555                 560
Asp Ala Leu Ala Leu Pro Thr Arg Tyr Leu Pro Lys Tyr Glu His Leu
                565                 570                 575
Asp Ala Lys Tyr Phe Pro Lys Asn
            580

<210> SEQ ID NO 7
<211> LENGTH: 591
<212> TYPE: PRT
<213> ORGANISM: Rhizobium meliloti
```

-continued

<220> FEATURE:
<223> OTHER INFORMATION: strain 1021

<400> SEQUENCE: 7

```
Met Lys Met Thr Thr Glu Glu Ala Phe Val Lys Val Leu Gln Met His
1               5                   10                  15

Gly Ile Glu His Ala Phe Gly Ile Ile Gly Ser Ala Met Met Pro Val
            20                  25                  30

Ser Asp Leu Phe Pro Lys Ala Gly Ile Arg Phe Trp Asp Cys Ala His
        35                  40                  45

Glu Thr Asn Ala Gly Met Met Ala Asp Gly Phe Ser Arg Ala Thr Gly
    50                  55                  60

Thr Met Ser Met Ala Ile Gly Gln Asn Gly Pro Gly Val Thr Gly Phe
65                  70                  75                  80

Ile Thr Ala Met Lys Thr Ala Tyr Trp Asn His Thr Pro Leu Leu Met
                85                  90                  95

Val Thr Pro Gln Ala Ala Asn Lys Thr Ile Gly Gln Gly Gly Phe Gln
            100                 105                 110

Glu Val Asp Gln Met Ala Met Phe Glu Glu Met Val Cys Tyr Gln Glu
        115                 120                 125

Glu Val Arg Asp Pro Ser Arg Ile Pro Glu Val Leu Asn Arg Val Ile
    130                 135                 140

Glu Lys Ala Trp Arg Gly Cys Ala Pro Ala Gln Ile Asn Ile Pro Arg
145                 150                 155                 160

Asp Phe Trp Thr Gln Val Ile Asp Val Asp Leu Pro Arg Ile Val Arg
                165                 170                 175

Phe Glu Arg Pro Ala Gly Gly Pro Ala Ile Ala Gln Ala Ala Arg
            180                 185                 190

Leu Leu Ser Glu Ala Lys Phe Pro Val Ile Leu Asn Gly Ala Gly Val
        195                 200                 205

Val Ile Gly Asn Ala Ile Gln Glu Ser Met Ala Leu Ala Glu Lys Leu
    210                 215                 220

Asp Ala Pro Val Cys Cys Gly Tyr Gln His Asn Asp Ala Phe Pro Gly
225                 230                 235                 240

Ser His Arg Leu Ser Val Gly Pro Leu Gly Tyr Asn Gly Ser Lys Ala
                245                 250                 255

Ala Met Glu Leu Ile Ser Lys Ala Asp Val Val Leu Ala Leu Gly Thr
            260                 265                 270

Arg Leu Asn Pro Phe Ser Thr Leu Pro Gly Tyr Gly Ile Asp Tyr Trp
        275                 280                 285

Pro Lys Asp Ala Ala Ile Ile Gln Val Asp Ile Asn Ala Asp Arg Ile
    290                 295                 300

Gly Leu Thr Lys Lys Val Thr Val Gly Ile Cys Gly Asp Ala Lys Gln
305                 310                 315                 320

Val Ala Gln Gln Ile Leu Gln Leu Ala Pro Ala Ala Gly Asp Ala
                325                 330                 335

Ser Arg Glu Glu Arg Lys Ala Leu Val His Gln Thr Arg Ser Ala Trp
            340                 345                 350

Leu Gln Gln Leu Ser Ser Met Asp His Glu Asp Asp Pro Gly Thr
        355                 360                 365

Glu Trp Asn Val Gly Ala Arg Gln Arg Glu Pro Asp Arg Met Ser Pro
    370                 375                 380

Arg Gln Val Trp Arg Ala Ile Gln Ala Val Leu Pro Lys Glu Ala Ile
385                 390                 395                 400
```

```
Ile Ser Thr Asp Ile Gly Asn Cys Ala Ile Gly Asn Ala Tyr Pro
            405                 410                 415

Ser Phe Glu Gln Gly Arg Lys Tyr Leu Ala Pro Gly Met Phe Gly Pro
        420                 425                 430

Cys Gly Tyr Gly Phe Pro Ser Ile Val Gly Ala Lys Ile Gly Cys Pro
        435                 440                 445

Asp Val Pro Val Val Gly Phe Ala Gly Asp Gly Ala Phe Gly Ile Ser
        450                 455                 460

Met Asn Glu Met Thr Ser Ile Gly Arg Glu Gly Trp Pro Ala Ile Thr
465                 470                 475                 480

Met Val Ile Phe Arg Asn Tyr Gln Trp Gly Ala Glu Lys Arg Asn Thr
                485                 490                 495

Thr Leu Trp Tyr Asp Asn Asn Phe Val Gly Thr Glu Leu Asn Pro Asn
            500                 505                 510

Leu Ser Tyr Ala Lys Val Ala Asp Gly Cys Gly Leu Lys Gly Val Thr
        515                 520                 525

Val Asp Thr Pro Ala Ala Leu Thr Glu Ala Leu Ala Lys Ala Ile Glu
        530                 535                 540

Asp Gln Ala Lys Gly Ile Thr Thr Phe Val Glu Val Leu Asn Gln
545                 550                 555                 560

Glu Leu Gly Glu Pro Phe Arg Arg Asp Ala Met Lys Lys Pro Val Ala
                565                 570                 575

Val Ala Gly Ile Asp Arg Ala Asp Met Arg Thr Gln Arg Met
            580                 585                 590

<210> SEQ ID NO 8
<211> LENGTH: 603
<212> TYPE: PRT
<213> ORGANISM: Roseovarius nubinhibens

<400> SEQUENCE: 8

Met Leu Phe Arg Ala Ser Gln Pro Glu Asp Lys Pro Met Lys Met Thr
1               5                   10                  15

Thr Glu Glu Ala Phe Val Lys Thr Leu Gln Met His Gly Ile Gln His
                20                  25                  30

Ala Phe Gly Ile Ile Gly Ser Ala Met Met Pro Ile Ser Asp Ile Phe
            35                  40                  45

Gly Lys Ala Gly Ile Thr Phe Trp Asp Cys Ala His Glu Gly Ser Gly
        50                  55                  60

Gly Met Met Ala Asp Gly Tyr Thr Arg Ala Thr Gly Lys Met Ser Met
65                  70                  75                  80

Met Ile Ala Gln Asn Gly Pro Gly Ile Thr Asn Phe Val Thr Ala Val
                85                  90                  95

Lys Thr Ala Tyr Trp Asn His Thr Pro Leu Leu Leu Val Thr Pro Gln
            100                 105                 110

Ala Ala Asn Lys Thr Met Gly Gln Gly Gly Phe Gln Glu Val Glu Gln
        115                 120                 125

Met Ala Ala Phe Lys Asp Met Val Cys Tyr Gln Glu Glu Val Arg Asp
    130                 135                 140

Pro Thr Arg Met Ala Glu Val Leu Asn Arg Val Ile Leu Asn Ala Lys
145                 150                 155                 160

Arg Tyr Ser Ala Pro Ala Gln Ile Asn Val Pro Arg Asp Tyr Phe Thr
                165                 170                 175

Gln Val Ile Asp Ile Glu Leu Pro Lys Ile Val Asp Phe Glu Arg Pro
```

-continued

```
                180                 185                 190
Ser Gly Gly Glu Glu Ala Leu Asp Glu Ala Ala Lys Leu Leu Ser Glu
            195                 200                 205
Ala Lys Phe Pro Val Ile Leu Asn Gly Ala Gly Val Ile Leu Ala Gly
        210                 215                 220
Ala Ile Pro Ala Thr Ala Glu Leu Ala Glu Arg Leu Asp Ala Pro Val
225                 230                 235                 240
Cys Cys Gly Tyr Gln His Asn Asp Ala Phe Pro Gly Ser His Pro Leu
                245                 250                 255
His Ala Gly Pro Leu Gly Tyr Asn Gly Ser Lys Ala Gly Met Glu Leu
            260                 265                 270
Ile Ser Lys Ala Asp Val Val Leu Ala Leu Gly Thr Arg Leu Asn Pro
        275                 280                 285
Phe Ser Thr Leu Pro Gly Tyr Gly Ile Asp Tyr Trp Pro Lys Asp Ala
290                 295                 300
Lys Ile Ile Gln Val Asp Val Lys Pro Glu Arg Ile Gly Leu Thr Lys
305                 310                 315                 320
Pro Val Ala Val Gly Ile Val Gly Asp Ala Lys Lys Val Ala Lys Thr
                325                 330                 335
Ile Leu Ala Lys Leu Ser Asp Thr Ala Gly Asp Ala Asp Arg Glu Glu
            340                 345                 350
Arg Lys Ala Thr Ile Ala Lys Thr Lys Ser Ala Trp Ala Gln Glu Leu
        355                 360                 365
Ser Ser Met Asp His Glu Gln Asp Asp Pro Gly Thr Thr Trp Asn Glu
    370                 375                 380
Arg Ala Arg Gly Ala Lys Pro Asp Trp Met Ser Pro Arg Met Ala Trp
385                 390                 395                 400
Arg Ala Ile Gln Ala Ala Leu Pro Lys Glu Ala Ile Ile Ser Ser Asp
                405                 410                 415
Ile Gly Asn Asn Cys Ala Ile Gly Asn Ala Tyr Pro Ser Phe Glu Glu
            420                 425                 430
Gly Arg Lys Tyr Leu Ala Pro Gly Leu Phe Gly Pro Cys Gly Tyr Gly
        435                 440                 445
Leu Pro Ala Val Val Gly Ala Lys Ile Gly Cys Pro Asp Thr Pro Val
    450                 455                 460
Val Gly Phe Ser Gly Asp Gly Ala Phe Gly Ile Ala Val Asn Glu Leu
465                 470                 475                 480
Thr Ala Ile Gly Arg Gly Glu Trp Pro Ala Val Thr His Val Val Phe
                485                 490                 495
Arg Asn Tyr Gln Trp Gly Ala Glu Lys Arg Asn Ser Thr Leu Trp Phe
            500                 505                 510
Asp Asp Asn Phe Val Gly Thr Glu Leu Asp Glu Gln Val Ser Tyr Ala
        515                 520                 525
Gly Ile Ala Lys Ala Cys Gly Leu Lys Gly Val Val Ala Arg Thr Met
    530                 535                 540
Asp Glu Leu Thr Asp Ala Leu Asp Gln Ala Ile Lys Asp Gln Lys Ala
545                 550                 555                 560
Gly Thr Thr Thr Leu Ile Glu Ala Met Ile Asn Gln Glu Leu Gly Glu
                565                 570                 575
Pro Phe Arg Arg Asp Ala Met Lys Lys Pro Val Ala Val Ala Gly Ile
            580                 585                 590
Asp Pro Ala Asp Met Arg Glu Gln Gln Val Asp
        595                 600
```

```
<210> SEQ ID NO 9
<211> LENGTH: 7
<212> TYPE: PRT
<213> ORGANISM: Unknown
<220> FEATURE:
<223> OTHER INFORMATION: Consensus sequence derived from alignment of
      protein from multiple species

<400> SEQUENCE: 9

Glu Gly Gly Glu Leu Gly Tyr
1               5

<210> SEQ ID NO 10
<211> LENGTH: 19
<212> TYPE: PRT
<213> ORGANISM: Unknown
<220> FEATURE:
<223> OTHER INFORMATION: Consensus sequence derived from alignment of
      protein from multiple species
<220> FEATURE:
<221> NAME/KEY: VARIANT
<222> LOCATION: (2)..(4)
<223> OTHER INFORMATION: Xaa can be any naturally occuring amino acid
<220> FEATURE:
<221> NAME/KEY: VARIANT
<222> LOCATION: (5)..(5)
<223> OTHER INFORMATION: Xaa can be Asp or Asn
<220> FEATURE:
<221> NAME/KEY: VARIANT
<222> LOCATION: (6)..(6)
<223> OTHER INFORMATION: Xaa can be any naturally occuring amino acid
<220> FEATURE:
<221> NAME/KEY: VARIANT
<222> LOCATION: (8)..(9)
<223> OTHER INFORMATION: Xaa can be any naturally occuring amino acid
<220> FEATURE:
<221> NAME/KEY: VARIANT
<222> LOCATION: (10)..(10)
<223> OTHER INFORMATION: Xaa can be Leu, Ile, Val, Phe, or Thr
<220> FEATURE:
<221> NAME/KEY: VARIANT
<222> LOCATION: (11)..(13)
<223> OTHER INFORMATION: Xaa can be any naturally occuring amino acid
<220> FEATURE:
<221> NAME/KEY: VARIANT
<222> LOCATION: (14)..(14)
<223> OTHER INFORMATION: Xaa can be Leu, Ile, Val, or Met
<220> FEATURE:
<221> NAME/KEY: VARIANT
<222> LOCATION: (15)..(15)
<223> OTHER INFORMATION: Xaa can be any naturally occuring amino acid

<400> SEQUENCE: 10

Gly Xaa Xaa Xaa Xaa Xaa Pro Xaa Xaa Xaa Xaa Xaa Xaa Xaa Xaa Gly
1               5                   10                  15

Asp Gly Glu
```

ENZYMATIC PRODUCTION OF ACETYL PHOSPHATE FROM FORMALDEHYDE

CROSS-REFERENCE TO RELATED APPLICATIONS

This application is a § 371 National Stage Application of PCT/EP2015/055254, filed 13 Mar. 2015, which claims priority to EP 14161723.3, filed 26 Mar. 2014 and EP 14176885.3, filed 14 Jul. 2014. All of these documents (PCT/EP2015/055254, EP 14161723.3 and EP 14176885.3) are hereby incorporated by reference in their entirety.

The present invention relates to a method for the enzymatic production of acetyl phosphate from formaldehyde said method making use of a phosphoketolase or of a sulfoacetaldehyde acetyltransferase, as well as to the use of a phosphoketolase or of a sulfoacetaldehyde acetyltransferase or of a microorganism expressing a phosphoketolase or a sulfoacetaldehyde acetyltransferase for the production of acetyl phosphate from formaldehyde.

For the past several decades, practitioners of metabolic engineering have endeavoured to explore biological solutions for the production of chemicals, thus, providing alternatives to more traditional chemical processes. In general, biological solutions allow for the utilization of renewable feedstocks (e.g. sugars) and compete with existing petrochemical based processes. A multi-step, biological solution for the production of a chemical typically comprises a microorganism as the catalyst for the conversion of feedstock to a target molecule. A complete set of enzyme reactions for the production of a particular target molecule can be grouped into those belonging to central carbon pathways and those belonging to the product specific pathway. The reactions belonging to central carbon and product specific pathways are linked in that redox (typically, NAD(P)H) and energetic (typically, ATP) constraints of every enzyme reaction must be accounted for in an overall balance contributing to the competitiveness of the process. Historically, central carbon pathways of heterotrophs growing on sugars have been described as the Embden-Meyerhoff-Parnas pathway (EMPP; i.e., "glycolysis"), the pentose phosphate pathway (PPP), the Entner-Doudoroff pathway (EDP), and the phosphoketolase pathway (PKP) (see Gottschalk (1986), Bacterial Metabolism, $2^{nd}$ Edition, Springer-Verlag, New York). Each central pathway or combinations of central pathways offer advantages and disadvantages with respect to a specific target molecule. In order to provide competitive bioprocesses, recombinant microorganisms with modifications involving the EMPP, PPP and EDP have been described (M. Emmerling et al., Metab. Eng. 1:117 (1999); L. O. Ingram et al., Appl. Environ. Microbiol. 53: 2420 (1987); C. T. Trinh et al., Appl. Environ. Microbiol. 74:3634 (2008)). More recently, recombinant microorganisms with modifications involving the PKP have been described (see Sonderegger et al. Appl. Environ. Microbiol. 70 (2004), 2892-2897, U.S. Pat. No. 7,253,001, Chinen et al. J. Biosci. Bioeng. 103 (2007), 262-269, U.S. Pat. No. 7,785,858; Fleige et al., Appl. Microbiol. Cell Physiol. 91 (2011), 769-776).

The EMPP (glycolysis) converts 1 mol glucose to 2 mol pyruvate (PYR). When acetyl-CoA is desired, 1 mol PYR can be converted to 1 mol of acetyl-CoA (AcCoA) with the concomitant generation of 1 mol $CO_2$ and 1 mol NADH. The sum of the reactions is given in Equation 1.

(Equation 1)

The PPP provides a means to convert 1 mol glucose to 1 mol $CO_2$ and 2 mol NADPH, with the concomitant generation of 0.67 mol fructose-6-phosphate (F6P) and 0.33 mol glyceraldehyde-3-phosphate (GAP). The F6P and GAP thus formed must be metabolized by other reaction pathways, e.g. by the EMPP. The EDP converts 1 mol glucose to 1 mol GAP and 1 mol PYR with the concomitant generation of 1 mol NADPH. As with the PPP, the GAP thus formed must be metabolized by other reaction pathways. The PKP provides a means to convert 1 mol glucose to 1 mol GAP and 1.5 mol acetyl phosphate (AcP). When acetyl-CoA is desired, 1 equivalent of AcP plus 1 equivalent coenzyme A (CoA) can be converted to 1 equivalent acetyl-CoA and 1 equivalent inorganic phosphate (Pi) by the action of phosphotransacetylase.

Various approaches have been described in the art for genetically modifying microorganisms so as to be able to convert various feedstocks such as liquefied cornflour, glycerol or syngas (a mixture of hydrogen and carbon monoxide) or compounds such as methane into desired compounds, such as liquid fuels or butanol (see, e.g., WO2012/053905 and Peralta-Yahya et al., Nature 488 (2012), 320-328). Conrado and Gonzalez (Science 343 (2014), 621-623) discuss, for example, possible options for converting methane into liquid fuels and mention in this context that methanotrophs can convert formaldehyde into pyruvate either through the ribulose monophosphate (RuMP) cycle, which uses formaldehyde directly, or through the Calvin-Benson-Bassham-(CBB) $CO_2$-fixation cycle from fully oxidized formaldehyde. However, the efficiency of such processes is said to be low and the processes are said to involve high metabolic energy losses.

In view of the increasing demand for processes which make use of renewable resources for producing all sorts of compounds, it is desirable to provide means and methods which allow for an efficient production of central metabolites, such as acetyl-CoA, or their precursors, thereby building a platform for developing further processes to convert these metabolites into useful compounds.

Thus, there is a need to provide methods, comprising central carbon and product specific pathways, that maximize the conversion of feedstock to product by best accommodating the redox and energetic constraints of enzyme reactions, thereby allowing the energetically efficient production of precursors of acetyl-CoA, one of the most central metabolites in catabolism of many organisms, in particular of microorganisms which can be used for the production of numerous industrially important compounds from renewable resources. Applicants have addressed this need by providing the embodiments as defined in the claims.

There is a need to provide methods allowing the energetically efficient production of precursors of acetyl-CoA, one of the most central metabolites in catabolism of many organisms, in particular of microorganisms which can be used for the production of numerous industrially important compounds from renewable resources. The present invention addresses this need by providing the embodiments as defined in the claims.

Thus, the present invention relates to method for the production of acetyl phosphate from formaldehyde by making use of a phosphoketolase or of a sulfoacetaldehyde acetyltransferase.

The present inventor surprisingly found that enzymes which are classified as phosphoketolases are capable of catalyzing the formation of acetyl phosphate from formaldehyde and phosphate according to the following reaction scheme:

$$2CH_2O + \text{phosphate} \rightarrow \text{acetyl phosphate} + H_2O$$

This reaction is strongly exergonic, dissipating more energy than ATP hydrolysis under physiological conditions.

Different types of phosphoketolases are known and all of them can be employed in the method according to the invention. Generally, phosphoketolases are classified into two types based on substrate preference as regards their naturally catalyzed reaction: xylulose-5-phosphate (X5P) phosphoketolases, which are classified in EC 4.1.2.9 and which naturally use X5P and fructose-6-phosphate (F6P) as a substrate but which prefer X5P, and X5P/fructose-6-phosphate (F6P) phosphoketolases, which are classified in 4.1.2.22 and which can use both X5P and F6P with comparable activities as substrate (Suzuki et al., J. Biol. Chem. 44 (2010), 34279-34287). In the following, the term "phosphoketolase" always refers to both types.

Thus, X5P phosphoketolases are enzymes which are classified in EC 4.1.2.9 and which are capable of catalyzing the following reaction:

$$\text{D-xylulose-5-phosphate} + \text{phosphate} \rightarrow \text{D-glyceraldehyde-3-phosphate} + \text{acetyl-phosphate} + H_2O$$

The other type of phosphoketolases which are classified in EC 4.1.2.22 are generally referred to as fructose-6-phosphate phosphoketolases and are naturally capable of catalyzing the following reaction:

$$\text{D-Fructose-6-phosphate} + \text{phosphate} \rightarrow \text{acetyl phosphate} + \text{D-erythrose 4-phosphate} + H_2O$$

There are also cases in which a phosphoketolase is assigned to both types of phosphoketolases, e.g., in the case of the phosphoketolase from *Nitrolancetus hollandicus* Lb, or where an identified phosphoketolase has not yet been assigned to any of the two types but is simply generally classified as a phosphoketolases. The term "phosphoketolase" when used herein also refers to all these phosphoketolases.

Thus, in one embodiment of the method according to the present invention the enzymatic conversion of formaldehyde and phosphate into acetyl phosphate according to the above shown reaction scheme is achieved by making use of a phosphoketolase which is classified as a phosphoketolases in EC 4.1.2.9. This enzyme has been identified in a variety of organisms, in particular microorganisms such as bacteria and fungi. In one preferred embodiment the phosphoketolase (EC 4.1.2.9) originates from a prokaryotic organism, preferably a bacterium. The enzyme has, for example, been described to occur in *Lactococcus lactis*, *Lactobacillus plantarum* (Uniprot Accession numbers: Q88S87; Q88U67), *Lactobacillus pentosus* (Uniprot Accession number: Q937F6), *Lactobacillus reuteri*, *Bifidobacterium animalis* (Uniprot Accession number: A0PAD9), *Bifidobacterium animalis* subsp. *lactis* (Uniprot Accession number: Q9AEM9), *Butyrovibrio fibrisolvens*, *Fibrobacter intestinalis*, *Fibrobacter succinogenes*, *Leuconostoc mesenteroides*, *Oenococcus oeni*, *Starkeya novella*, *Thiobacillus* sp., *Thermobispora bispora* (strain ATCC 19993/DSM 43833/CBS 139.67/JCM 10125/NBRC 14880/R51; Uniprot Accession number D6YAD9), *Thermobaculum terrenum* (strain ATCC BAA-798/YNP1; Uniprot Accession number D1CI63) and *Nitrolancetus hollandicus* Lb (Uniprot Accession number I4EJ52).

In another preferred embodiment the phosphoketolase (EC 4.1.2.9) originates from a eukaryotic organism, preferably a fungus, e.g. a yeast, such as *S. cerevisiae*. The enzyme has, for example, been described to occur in *Emericella nidulans* (Uniprot Accession number: Q5B3G7), *Metarhizium anisopliae* (Uniprot Accession number: C1K2N2), *Candida boidinii*, *Candida curvata*, *Candida famata*, *Candida humicola*, *Candida parapsilosis*, *Candida parapsilosis* NCYC 926, *Candida tropicalis*, *Cyberlindnera jadinii*, *Cyberlindnera saturnus*, *Debaromyces robertsiae*, *Fusarium oxysporum*, *Kluyveromyces marxianus*, *Kluyveromyces phaseolosporus*, *Lipomyces starkeyi*, *Ogataea angusta*, *Pachysolen tannophilus*, *Priceomyces medius*, *Saccharomyces cerevisiae*, *Rhodospiridium toruloides*, *Rhodotorula glutinis*, *Rhodotorula graminis*, *Penicillium chrysogenum*, *Trichosporon cutaneum* and *Yarrowia lipolytica*.

The enzymatic activity of a phosphoketolase (EC 4.1.2.9) can be assessed with methods known to a person skilled in the art. Such methods are, e.g., described in Meile et al. (J. Bacteriol. 183 (2001), 2929-2936) and in Suzuki et al (Acta Cryst. F66 (2010), 941-943).

The phosphoketolase (EC 4.1.2.9) is structurally and functionally well defined. For example, Petrareanu et al. (Acta Crystallographica F66 (2010), 805-807) describe the X-ray crystallographic analysis of the xylulose-5-phosphate phosphoketolase from *Lactococcus lactis*.

In another embodiment of the method according to the present invention the enzymatic conversion of formaldehyde and phosphate into acetyl phosphate according to the above shown reaction scheme is achieved by making use of a phosphoketolase which is classified as a fructose-6-phosphate phosphoketolase in EC 4.1.2.22. This enzyme has been identified in a variety of organisms, in particular microorganisms such as bacteria and fungi. In one preferred embodiment the fructose-6-phosphate phosphoketolase (EC 4.1.2.22) originates from a prokaryotic organism, preferably a bacterium. The enzyme has, for example, been described to occur in *Bifidobacterium adolescentis*, *Bifidobacterium animalis* subsp. *lactis* (Uniprot Accession number: Q9AEM9), *Bifidobacterium longum*, *Bifidobacterium pseudolongum*, in particular *Bifidobacterium pseudolongum* subsp. *globosum*, *Bifidobacterium bifidum*, *Bifidobacterium breve*, *Bifidobacterium dentium*, *Bifidobacterium mongoliense*, *Bifidobacterium bombi*, *Cupriavidus necator*, *Gardnerella vaginalis*, *Gluconacetobacter xylinus*, *Lactobacillus paraplantarum*, *Leuconostoc mesenteroides* and *Nitrolancetus hollandicus* Lb (Uniprot Accession number I4EJ52).

In another preferred embodiment the fructose-6-phosphate phosphoketolase (EC 4.1.2.22) originates from a eukaryotic organism, preferably a fungus, e.g. a yeast, such as *S. pastorianus*. The enzyme has, for example, been described to occur in *Candida* sp., *Candida* sp. 107, *Candida tropicalis*, *Rhodotorula glutinis*, *Rhodotorula graminis* and *Saccharomyces pastorianus*.

The enzyme is structurally and functionally well defined. For example, Suzuki et al. (Acta Crystallographica F66 (2010), 941-943; J. Biol. Chem. 285 (2010), 34279-34287) describe the overexpression, crystallization and X-ray analysis of the phosphoketolase from *Bifidobacterium breve*. The gene encoding the xylulose-5-phosphate/fructose-6-phosphate phosphoketolase from *Bidifobacterium lactis* is e.g. described in Meile et al. (J. Bacteriol. 183 (2001), 2929-2936).

The enzymatic activity of a fructose-6-phosphate phosphoketolase (EC 4.1.2.22) can be assessed with methods known to a person skilled in the art. Such methods are, e.g., described in Meile et al. (J. Bacteriol. 183 (2001), 2929-2936) and in Suzuki et al. (Acta Cryst. F66 (2010), 941-943).

Other phosphoketolases which have not yet been classified into EC 4.2.1.9 or EC 4.2.1.22 and which can be used in the method according to the present invention are, e.g. the phosphoketolase from *Thermosynechococcus elongatus* (strain BP-1; Uniprot Accession number: Q8DJN6), the phosphoketolase from *Bacillus coagulans* 36D1 (Uniprot Accession number: G2TIL0), the phosphoketolase from *Lactococcus lactis* subsp. *lactis* (Strain KF147; Uniprot Accession number: A9QST6; SEQ ID NO: 3), the phosphoketolase from *Bifidobacterium pseudolongum* subsp. *globosum* (Uniprot Accession number: Q6R2Q6; SEQ ID NO: 1) and the phosphoketolase from *Clostridium acetobutylicum* (Strain ATCC 824; Uniprot Accession number: Q97JE3; Servisky et al. (J. Ind. Microbiol. Biotechnol. 39 (2012), 1859-1867); SEQ ID NO: 2).

In the appended Examples it is shown that the phosphoketolases of *Bifidobacterium pseudolongum* subsp. *globosum* (Uniprot Accession number: Q6R2Q6; SEQ ID NO: 1), of *Clostridium acetobutylicum* (Strain ATCC 824; Uniprot Accession number: Q97JE3; SEQ ID NO: 2) and of *Lactococcus lactis* subsp. *lactis* (Strain KF147; Uniprot Accession number: A9QST6; SEQ ID NO: 3) are capable of converting formaldehyde and phosphate into acetyl phosphate and $H_2O$.

In a preferred embodiment, the phosphoketolase employed in the method of the invention has an amino acid sequence as shown in any one of SEQ ID NOs: 1 to 3 or shows an amino acid sequence which is at least x % homologous to any one of SEQ ID NOs: 1 to 3 and has the activity of a phosphoketolase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting formaldehyde and phosphate into acetyl phosphate as set forth herein above.

Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

It has been described that a multiple alignment of phosphoketolase sequences shows several highly conserved regions and two of these regions are used as signature patterns for phosphoketolases (prosite.expasy.org/PDOC60002). The first signature pattern is E-G-G-E-L-G-Y (SEQ ID NO:9) and the second signature pattern is G-x(3)-[DN]-x-P-x(2)-[LIVFT]-x(3)-[LIVM]-x-G-D-G-E (SEQ ID NO:10). The function of the first signature pattern is not yet known while the second signature pattern corresponds to the thiamine pyrophosphate binding site. Thus, in a preferred embodiment, a phosphoketolase as defined herein above has an amino acid sequence which contains at least one of the two above mentioned signature patterns, preferably at least the second signature pattern, and even more preferably both signature patterns.

Sequence comparisons show that the overall sequence identity between phosphoketolases from different origins can be as low as around 26%. For example, Meile et al. (J. Biol. Chem. 183 (2001), 2929-2936) reports that the D-xylulose 5-phosphate/D-fructose 6-phosphate phosphoketolase gene (xfp) of *Bifidobacterium lactis* revealed identities of 26% to 55% to sequences in the genomes of other organisms.

Whether a chosen phosphoketolase is capable of catalyzing the conversion of formaldehyde and phosphate into acetyl phosphate and $H_2O$ can, e.g., be assessed by an assay as set forth in the appended Examples.

The term "phosphate" as used in connection with the method of the invention refers to a compound which is acceptable as a phosphate source for the enzyme employed in the method for the conversion of formaldehyde and phosphate into acetyl phosphate and $H_2O$. One possibility is the provision of phosphate in the form of phosphoric acid, i.e. $H_3PO_4$. However, also other forms are conceivable, in particular salts of phosphoric acid ($H_3PO_4$) in which one, two or three of the hydrogen atoms are replaced by other ions, such as sodium ions. Phosphoketolases are thiamine diphosphate-dependent enzymes, i.e. they require thiamine diphosphate (also referred to as ThDP or TPP) as a cofactor. Therefore, it is advantageous that in a method according to the invention TPP is provided during the reaction. Moreover, some phosphoketolases require ions, such as $Mg^{2+}$ or $Ca^{2+}$ as cofactors. In such a case, the method according to the invention also includes the presence of such ions during the conversion as described above.

The enzymatic conversion of formaldehyde and phosphate into acetyl phosphate according to the above shown reaction scheme can also be achieved by making use of a sulfoacetaldehyde acetyltransferase (EC 2.3.3.15). Sulfoacetaldehyde acetyltransferases (EC 2.3.3.15) are enzymes which can catalyze the following reaction:

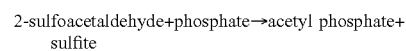
2-sulfoacetaldehyde+phosphate→acetyl phosphate+ sulfite

The enzyme has been identified in a variety of organisms, in particular bacteria. In one preferred embodiment the sulfoacetaldehyde acetyltransferase (EC 2.3.3.15) originates from a prokaryotic organism, preferably a bacterium. The enzyme has, for example, been described to occur in *Castellaniella defragans* (Uniprot Accession number: Q84H44; previously *Alcaligenes defragans* (Ruff et al., Biochem. J. 369 (2003), 275-285)), *Alcaligenes xylosoxydans xylosoxydans* (Uniprot Accession number: Q84H41), *Desulfonispora thiosulfatigenes* (Uniprot Accession number: Q93PS3), *Rhizobium meliloti* (strain 1021) (Uniprot Accession number: Q92UW6), *Ruegeria pomeroyi* (Uniprot Accession number: Q5LMK2), *Cupriavidus necator* (Uniprot Accession number: Q0K022), *Roseovarius nubinhibens* (Uniprot Accession number: A3SR25), *Acinetobacter* sp. and *Pseudomonas aeruginosa*.

In principle any sulfoacetaldehyde acetyltransferase (EC 2.3.3.15) can be employed in the conversion of formaldehyde and phosphate into acetyl phosphate according to a method of the invention.

Sulfoacetaldehyde acetyltransferases are, like phosphoketolases, thiamine pyrophosphate (TPP)-dependent enzymes and therefore are characterized in that they contain a TPP binding domain. Among the sulfoacetaldehyde acetyltransferases known, the TPP binding domain is highly conserved (see, e.g., Ruff et al., Biochem. J. 369 (2003), 275-285). Overall, the known sulfoacetaldehyde acetyltransferases show a high degree of sequence conservation near the N-terminus, including the TPP binding domain (see Ruff et al., loc. cit.). Sequence divergence can be observed in the N-terminus of the enzymes itself and in a region near amino acid 400 of the *C. defragans* enzyme. Ruff et al. (loc. cit.) describe that sulfoacetaldehyde acetyltransferases form 3 subgroups (see FIG. 4 of said publication). Subgroups 2 and 3 are said to show a TPP binding domain conforming with the PROSITE consensus sequence (L/I/V/M/F)(G/S/A)X$_5$PX$_4$(L/I/V/M/F/Y/W)X(L/I/V/M/F)XGD(G/S/A)(G/S/A/C), while subgroup slightly deviates from the consensus sequence: (L/I/V/M/F)(G/S/A)X$_5$PX$_4$(L/I/V/M/F/Y/W)X(L/1/V/M/F/Y)XGD(G/S/A)(G/S/A/C).

Apart from these regions, the sequence identity between the different sulfoacetaldehyde acetyltransferases can be rather low (down to about 44%).

In a preferred embodiment, the sulfoacetaldehyde acetyltransferase employed in a method according to the present invention is the sulfoacetaldehyde acetyltransferase of *C. defragans* showing the amino acid sequence as depicted in SEQ ID NO:4 or the sulfoacetaldehyde acetyltransferase of *Alcaligenes* xylosoxydans xylosoxydans showing the amino acid sequence as depicted in SEQ ID NO:5 or the sulfoacetaldehyde acetyltransferase of *Desulfonispora thiosulfatigenes* showing the amino acid sequence as depicted in SEQ ID NO:6 or the sulfoacetaldehyde acetyltransferase of *Rhizobium meliloti* (strain 1021) showing the amino acid sequence as depicted in SEQ ID NO:7 or the sulfoacetaldehyde acetyltransferase of *Roseovarius nubinhibens* showing the amino acid sequence as depicted in SEQ ID NO:8 or showing a related amino acid sequence.

Thus, in a preferred embodiment, the sulfoacetaldehyde acetyltransferase employed in the method of the invention has an amino acid sequence as shown in any one of SEQ ID NOs: 4 to 8 or shows an amino acid sequence which is at least x % homologous to any one of SEQ ID NOs: 4 to 8 and has the activity of a sulfoacetaldehyde acetyltransferase ith x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting formaldehyde and phosphate into acetyl phosphate as set forth herein above. Preferably, the degree of identity is determined as described above.

The enzymatic activity of a sulfoacetaldehyde acetyltransferase (EC 2.3.3.15) can be assessed with methods known to a person skilled in the art. Such methods are, e.g., described in Ruff et al. (Biochem. J. 369 (2003), 275-285).

The acetyl phosphate produced according to a method of the present invention can be further converted into desired molecules such as acetate or acetyl-Coenzyme A (also referred to as acetyl-CoA) which is a central metabolite in most organisms.

The hydrolysis of acetyl phosphate into acetate in vitro occurs spontaneously since acetyl phosphate is rather unstable.

Acetyl phosphate can also be converted, in vitro or in vivo, enzymatically into acetate, e.g. by making use of an acetate kinase (EC 2.7.2.1), a propionate kinase (EC 2.7.2.15), a butyrate kinase (EC 2.7.2.7) or an acetate kinase (diphosphate) (EC 2.7.2.12).

Acetate kinase is an enzyme which catalyzes the following reaction:

ATP+acetate ⇌ ADP+acetyl phosphate.

Since this reaction is reversible, the enzyme can be employed to convert acetyl phosphate into acetate. The reaction may be pushed into the direction of acetate by continuously removing ATP from the reaction, e.g. by further enzymatic conversion or by removal from the reaction by means and methods known to the person skilled in the art. This enzyme occurs in a large variety of organism, in particular in prokaryotes, eukaryotes and archae. It is an important enzyme in glycolysis and the enzyme levels are normally increased in the presence of excess glucose. In principle any acetate kinase (EC 2.7.2.1) can be used to convert acetyl phosphate into acetate in a method according to the invention.

Also propionate kinase (EC 2.7.2.15) has been described to be able to convert acetyl phosphate into acetate according to the reaction scheme:

ATP+acetate ⇌ ADP+acetyl phosphate.

This enzyme is found in Enterobacteriaceae, such as *E. coli* or *Salmonella* enteric subsp. *enterica serovar. thyphimurium*.

The conversion of acetyl phosphate into acetate can also be achieved by making use of a butyrate kinase (EC 2.7.2.7). Butyrate kinases are enzymes which catalyze the following reaction:

ATP+butanoate ⇌ ADP+butanoyl phosphate

However, it has been shown for some butyrate kinases, e.g. for those from *Clostridium butyricum* and from *Clostridium acetobutylicum*, that they can also catalyze the reaction:

ATP+acetate ⇌ ADP+acetyl phosphate

Thus, any butyrate kinase which is also capable of catalyzing the reversible conversion of ATP+acetate into ADP+acetyl phosphate can be employed in a method of the present invention for converting acetyl phosphate into acetate.

Moreover, the conversion of acetyl phosphate into acetate can also be achieved by making use of an acetate kinase (diphosphate) (EC 2.7.2.12). Acetate kinases (diphosphate) (EC 2.7.2.12) are enzymes which catalyze the following reaction:

Diphosphate+acetate ⇌ H$_3$PO$_4$+acetyl phosphate.

This enzyme has been described to occur in *Entamoeba histolytica*.

The enzymatic hydrolysis of acetyl phosphate into acetate and H$_3$PO$_4$ can also be achieved by making use of an acylphosphatase (EC 3.6.1.7). Acylphosphatase (AcP; EC 3.6.1.7) is a cytosolic enzyme (with a molecular weight of about 10 kDa) widely expressed in eukaryotic and prokaryotic organisms (both mesophilic and extremophilic). AcP can be found in many tissues of vertebrate species in the skeletal muscles and in the heart as muscle-type AcP (MT-AcP) and in erythrocytes, brain and testis as (organ) common-type AcP (CT-AcP) (Zuccotti et al., Acta Cryst. 61 (2005), 144-146). Acylphosphatases catalyze the following reaction:

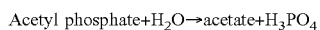
Acetyl phosphate+H$_2$O→acetate+H$_3$PO$_4$

This enzyme has been described in a large variety of organisms. Preferably, an acylphosphatase employed in a method according to the present invention is derived from *Gallus gallus, Cavia porcellus* (Liguri et al., Biochem. J. 217 (1984), 499-505), *Homo sapiens, Sus scrofa, Bos taurus, Oryctolagus cuniculus, Equus* acallus or *Pyrococcus hirokoshii* (Miyazoo et al., Acta Crystallographica D60 (2004), 1135-1136).

The structural and functional characteristics of these enzymes have already been studied in detail and are described, e.g., in Liguri et al. (Biochem. J. 217 (1984), 499-505), Miyazoo et al. (Acta Crystallographica D60 (2004), 1135-1136) and in Taddei et al. (FEBS Letters 362 (1995), 175-179).

The conversion of acetyl phosphate into acetyl-CoA (in vitro or in vivo) can be achieved enzymatically, e.g. by the use of phosphate acetyltransferase (EC 2.3.1.8). This enzyme naturally catalyzes the following reaction:

$$\text{acetyl-CoA} + H_3PO_4 \rightleftharpoons \text{CoA} + \text{acetyl phosphate}$$

The enzyme occurs in a multitude of organisms, i.e. in prokayotes, eukaryotes and archae. In principle any known phosphate acetyltransferase (EC 2.3.1.8) can be employed for this conversion.

The formaldehyde converted according to a method of the present invention into acetyl phosphate can be provided externally to the reaction or can be provided by another chemical or enzymatic reaction.

The chemical production of formaldehyde has been known for a long time and generally formaldehyde is industrially produced by the catalytic oxidation of methanol. The most common catalysts in this context are silver metal or a mixture of an iron and molybdenum or vanadium oxides. In the commonly used formox process, methanol and oxygen react at approximately 250 to 400° C. in the presence of iron oxide in combination with molybdenum and/or vanadium to produce formaldehyde according to the following chemical equation:

$$2CH_3OH + O_2 \rightarrow 2CH_2O + 2H_2O$$

The silver-based catalyst usually operates at a higher temperature, about 650° C. Two chemical reactions on it simultaneously produce formaldehyde: that shown above and the dehydrogenation reaction:

$$CH_3OH \rightarrow H_2CO + H_2$$

Formaldehyde can also be generated by oxidation of methane. Moreover, it has been described that formaldehyde (and methanol) can be produced by a reaction of carbon monoxide and hydrogen on neutral Fe2S2 clusters in gas phase (see Yin et al., Phys. Chem. Chem. Phys. 15 (2013), 4699-4706).

In a preferred embodiment a method of the present invention further comprises the step of providing the formaldehyde to be converted by the enzymatic conversion of methanol. Enzymes which catalyze the conversion of methanol into formaldehyde are known and include, e.g. methanol dehydrogenase (EC 1.1.1.244). Methanol dehydrogenase (EC 1.1.1.244) catalyzes the following reaction:

$$\text{Methanol} + NAD^+ \rightleftharpoons \text{formaldehyde} + NADH + H^+$$

This enzyme has been identified in the methylotrophic *Bacillus* species *Bacillus methanolicus* (Arfman et al., Arch. Microbiol. 152 (1989), 280-288). Enzymes which can also catalyze the conversion of methanol into formaldehyde are enzymes classified as EC 1.1.2.7 (methanol dehydrogenase (cytochrome c)). These enzymes are type II PQQ-containing alcohol dehydrogenases, i.e. NAD(P)-independent methanol dehydrogenases. Such enzymes are, for example, known from several proteobacteria such as *Methylobacterium extorquens, Methylophilus methylotrophus* or *Hyphomicrobium denitrificans*. Moreover, also alcohol oxidases (EC 1.1.3.13) can be employed for the conversion of methanol into formaldehyde. Alcohol oxidases (EC 1.1.3.13) are enzymes which catalyze the following reaction:

$$\text{Primary alcohol} + O_2 \rightarrow \text{aldehyde} + H_2O_2$$

These enzymes have been identified in a large variety of organisms, e.g., methylotrophic yeast such as *Pichia, Candida* and *Hansenula*, that use methanol as a sole carbon and energy source (Hartner and Glieder, Microbial Cell Factories 5 (2006), 39) and in some fungi, e.g. *Aspergillus* (Kumar and Goswami, Appl. Microbiol. Biotechnol. 72 (2006), 906-911). Arnaud et al. (FEBS 296 (1992), 259-262) describe that purified terminal oxidase of *Pseudomonas nautica* strain 617 reduces CO to formaldehyde.

The methanol which can be converted into formaldehyde can itself be provided by enzymatic reactions from methane. In particular, the conversion of methane to methanol is, e.g., catalyzed by methane monooxygenase (MMO). Two types of this enzyme have been described, i.e. EC 1.14.13.25 methane monooxygenase (soluble) and EC 1.14.18.3 methane monooxygenase (particulate). The catalyzed reactions are:

$$CH_4 + NADH + H^+ + O_2 \rightarrow CH_3OH + NAD + H_2O \text{ (with NADH as co-factor)}$$

$$CH_4 + NADPH + H^+ + O_2 \rightarrow CH_3OH + NADP + H_2O \text{ (with NADPH as co-factor)}$$

Corresponding enzymes have been identified, e.g., in methanotrophic bacteria such as *Methylococcus capsulatus* (Pilkington and Dalton, Methods Enzymology 188 (1990), 181-190) and *Methylosinus trichosporium* (Fox et al., J. Biol. Chem. 266 (1991), 540-550). These enzymes have been characterized by in vitro studies, including cristal structure analysis (Sazinsky et al., Biochemistry 43 (2004), 16263-16276).

The method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, co-substrates, co-factors etc.) allowing the enzymes to be active and the enzymatic conversion to occur. The reaction is allowed to proceed for a time sufficient to produce the respective product. The production of the respective products can be measured by methods known in the art, such as liquid chromatography (HPLC) possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

The Examples illustrate in vitro reactions according to the invention using phosphoketolases from different origins.

In another embodiment the method according to the invention is carried out in culture, in the presence of an organism, preferably a microorganism, producing at least a phosphoketolase or a sulfoacetaldehyde acetyltransferase and optionally enzymes which are necessary for providing formaldehyde or for further converting the produced acetyl phosphate into other compounds, such as acetate or acetyl-CoA, as described herein above. A method which employs a microorganism for carrying out a method according to the invention is referred to as an "in vivo" method. The formaldehyde may either be provided externally or may be produced by the employed microorganism expressing the phosphoketolase or the sulfoacetaldehyde acetyltransferase itself. Such a microorganism expresses at least one enzyme necessary for the enzymatic production of formaldehyde as described herein above. It is also possible to co-culture a microorganism which is capable of producing formaldehyde and a microorganism which expresses a phosphoketolase and/or a sulfoacetaldehyde acetyltransferase so as to convert the formaldehyde produced by the first microorganism.

Thus, in such embodiments of the invention, a microorganism that produces at least a phosphoketolase or a sulfoacetaldehyde acetyltransferase as described above is used. It is possible to use a microorganism which naturally produces the phosphoketolase or the sulfoacetaldehyde acetyltransferase or a microorganism which had been genetically modified so that it expresses (or overexpresses) a phosphoketolase and/or the sulfoacetaldehyde acetyltransferase. Thus, the microorganism can be a microorganism which naturally expresses a phosphoketolase and/or a sulfoacetaldehyde acetyltransferase, i.e. which naturally has in its genome a nucleotide sequence encoding a phosphoketolase or a sulfoacetaldehyde acetyltransferase and which expresses it/them. The expression may occur constitutively or in an induced or regulated manner. Microorganisms that inherently, i.e. naturally, have phosphoketolase activity or sulfoacetaldehyde acetyltransferase activity are known in the art and any of them can be used in the context of the present invention.

In another embodiment the microorganism can be a microorganism which has been genetically modified by the introduction of a nucleic acid molecule containing a nucleotide sequence encoding a phosphoketolase or a sulfoacetaldehyde acetyltransferase. The nucleic acid molecule can be stably integrated into the genome of the microorganism or may be present in an extrachromosomal manner, e.g. on a plasmid.

Such a genetically modified microorganism can, e.g., be a microorganism that does not naturally have phosphoketolase activity or sulfoacetaldehyde acetyltransferase activity and has been genetically modified to express a phosphoketolase or a sulfoacetaldehyde acetyltransferase or a microorganism which naturally has phosphoketolase activity or sulfoacetaldehyde acetyltransferase activity and which has been genetically modified, e.g. by transformation with a nucleic acid, e.g. a vector, encoding a phosphoketolase or a sulfoacetaldehyde acetyltransferase in order to increase the phosphoketolase activity or sulfoacetaldehyde acetyltransferase activity in said microorganism and/or by insertion of a promoter in front of the endogenous nucleotide sequence encoding the enzyme in order to increase the respective activity in said microorganism.

However, the invention preferably excludes naturally occurring microorganisms as found in nature expressing an enzyme as described above at levels as they exist in nature. Instead, the microorganism of the present invention and employed in a method of the present invention is preferably a non-naturally occurring microorganism, whether it has been genetically modified to express (including overexpression) an exogenous enzyme of the invention not normally existing in its genome or whether it has been engineered to overexpress an exogenous enzyme.

Thus, the enzymes and (micro)organisms employed in connection with the present invention are preferably non-naturally occurring enzymes or (microorganisms), i.e. they are enzymes or (micro)organisms which differ significantly from naturally occurring enzymes or microorganism and which do not occur in nature. As regards the enzymes, they are preferably variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein above which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

A "non-natural" substrate is understood to be a molecule that is not acted upon by the respective enzyme in nature, even though it may actually coexist in the microorganism along with the endogenous enzyme. This "non-natural" substrate is not converted by the microorganism in nature as other substrates are preferred (e.g. the "natural substrate"). Thus, the present invention contemplates utilizing a non-natural substrate with the enzymes described above in an environment not found in nature.

Thus, it is also possible in the context of the present invention that the microorganism is a microorganism which naturally does not have phosphoketolase activity or sulfoacetaldehyde acetyltransferase activity but which is genetically modified so as to comprise a nucleotide sequence allowing the expression of a phosphoketolase or a sulfoacetaldehyde acetyltransferase. Similarly, the microorganism may also be a microorganism which naturally has phosphoketolase activity or sulfoacetaldehyde acetyltransferase activity but which is genetically modified so as to enhance the phosphoketolase activity or sulfoacetaldehyde acetyltransferase activity, e.g. by the introduction of an exogenous nucleotide sequence encoding a phosphoketolase or a sulfoacetaldehyde acetyltransferase or by the introduction of a promoter for the endogenous gene encoding the enzyme to increase endogenous production to overexpressed (non-natural) levels.

If a microorganism is used which naturally expresses a phosphoketolase or a sulfoacetaldehyde acetyltransferase, it is possible to modify such a microorganism so that the respective activity is overexpressed in the mircroorganism. This can, e.g., be achieved by effecting mutations in the promoter region of the corresponding gene or introduction of a high expressing promoter so as to lead to a promoter which ensures a higher expression of the gene. Alternatively, it is also possible to mutate the gene as such so as to lead to an enzyme showing a higher activity.

By using microorganisms which express a phosphoketolase or a sulfoacetaldehyde acetyltransferase, it is possible to carry out the method according to the invention directly in the culture medium, without the need to separate or purify the enzymes.

In one embodiment the organism employed in the method according to the invention is a microorganism which has been genetically modified to contain a foreign nucleic acid molecule encoding a phosphoketolase or a sulfoacetaldehyde acetyltransferase. The term "foreign" or "exogenous" in this context means that the nucleic acid molecule does not naturally occur in said microorganism. This means that it does not occur in the same structure or at the same location in the microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of organisms, in particular in microorganisms, are well known to the person skilled in the art.

In a further embodiment the nucleic acid molecule is foreign to the microorganism in that the encoded enzyme is not endogenous to the microorganism, i.e. is naturally not expressed by the microorganism when it is not genetically modified. In other words, the encoded enzyme is heterologous with respect to the microorganism. The foreign nucleic acid molecule may be present in the microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis, Pichia pastoris, Pichia torula* or *Pichia utilis*.

In another embodiment, the method according to the invention makes use of a photosynthetic microorganism expressing at least a phosphoketolase and/or a sulfoacetaldehyde acetyltransferase. Preferably, the microorganism is a photosynthetic bacterium, or a microalgae. In a further embodiment the microorganism is an algae, more preferably an algae belonging to the diatomeae.

It is also conceivable to use in the method according to the invention a combination of microorganisms wherein different microorganisms express different enzymes as described above.

In a particularly preferred embodiment the microorganism employed in a method according to the present invention is a methanotrophic or methylotrophic bacterium or a methanotrophic or methylotrophic yeast. Such microorganisms are preferably employed in a method according to the present invention since they have naturally the capability of metabolizing methanol and/or methane in order to produce formaldehyde via the enzymatic reactions described herein above. Methanotrophic bacteria and their possible uses are, e.g. described in Jiang et al. (Biochemical Engineering J. 49 (2010), 277-288), Schrader et al. (Trends in Biotechnology 27 (2008), 107-115), Chistoserdova et al. (Anu. Rev. Microbiol. 63 (2009), 477-499) and Kalyuzhnaya et al. (Nature Commun. 4 (2013). The diversity of these bacteria is, e.g. described in Chistoserdova et al. (loc. cit.) and in Jiang et al. (loc. cit.). Schrader et al. (loc. cit.) and Kalyuzhnaya et al. (loc. cit.) describe the use of such microorganisms as catalysts for methane conversion. Finally, Schrader et al. (loc. cit.) also describe genetic tools allowing to manipulate the metabolism of methylotrophic bacteria (such as *Methylobacterium extorquens*) for the formation of a desired product. Examples of methanotroph or methylotrophic bacteria include but are not limited to bacteria of the family Methylophilaceae, and bacteria of the genus *Methylobacter, Methylobacterium* (e.g. *Methylobacterium extorquens Methylobacterium organophilum* and *Methylobacterium rhodesianum*), *Methylobacillus* (e.g. *Methylobacillus flagellatus* and *Methylobacillus glycogenes*), *Methylomonas* (e.g *Methylomonas methanica*), *Methylosoma, Methylomicrobium* (e.g. *Methylomicrobium alcaliphilum*), *Methylothermus, Methylohalobius, Methylosarcina, Methylosphaera, Methylocystis, Methylosinus* (e.g. *Methylosinus trichosporium*), Methylocapsa, *Methylocella, Methylococcus* (e.g. *Methylococcus capsulatus*), Methylocaldum, *Methylophilus* (e.g. *Methylophilus methylotrophus*), *Methylacidiphilum, Hyphomicrobium* (e.g. *Hyphomicrobium methylovorum* or *Hyphomicrobium zavarzinii*), *Bacillus* (e.g. *Bacillus methanolicus*), *Pseudomonas, Paracoccus* (e.g. *Paracoccus denitrificans*), *Silicibacter* (e.g. *Silicibacter pomeroyi*), or *Granulibacter* (e.g. *Granulibacter bethesdensis*).

In a preferred embodiment the microorganism employed in a method according to the present invention is a microorganism which expresses a methanol dehydrogenase (MDH) and in particular a pyrroloquinoline-quinone (PQQ)-containing enzyme (quinoprotein) which catalyzes the ocidation of methanol to formaldehyde (Anthony, Adv. Microbila Physiol. 27 (1986), 113-120; Duine and Frank, Methanol dehydrogenase: A quinoprotein; In: Microbial Growth on $C_1$ Compounds; Ed. Dalton, H., Heyden & Son Ltd., London (1981), 31-41; Duine et al., Eur. J. Biochem. 108 (1980), 187-192).

In a particularly preferred embodiment the microorganism employed in a method according to the present invention is a microorganism of the genus *Acidomonas*, preferably of the species *Acidomonas methanolica* (former name: *Acetobacter methanolicus*). *Acidomonas methanolica* is a unique acetic acid bacterium which is capable of growing on methanol as a sole carbon source. This bacterium is particularly useful in a method according to the present invention since it takes up methanol efficiently. The methanol is converted by such a bacterium into formaldehyde due to the expression of a methanol dehydrogenase (encoded by the MxaF gene; see, e.g. Suzuki et al., J. Gen. Appl. Microbiol. 55 (2009), 101-110). A draft genomic DNA sequence of this organism has been reorted by Higashiura et al. (FEMS Microbiol. Lett. 351 (2014), 9-13). The methanol dehydrogenase of *Acidomonas methanolica* is a quinoprotein and its properties have been described in detail (Frébortova et al., Biochim. Biophys. Acta 1363 (1998), 24-34).

Other examples are bacteria belonging to the Verrucomicrobia phylum or bacteria of the order Burkholderiales, in particular of the families Comamonadaceae or Rhodocyclaceae, e.g. of the genus *Methylibium* (e.g. *Methylibium petroleiphilum*) and *Burkholderia* (e.g. *Burkholderia phymatum*). Further examples are filamentous bacteria, for example of the genus *Crenothrix* (e.g. *Crenothrix polyspora*), of the genus *Clonothrix* (e.g. *Clonothrix fusca*) or of the genus *Beggiatoa* (e.g. *Beggiatoa alba*).

Methanotrophic or methylotrophic yeast include, e.g., yeasts of the genus *Pichia*, preferably *Pichia pastoris*), of the genus *Candida* (e.g. *Candida boidinii*), of the genus *Ogataea*, of the geus *Kuraishia*, of the genus *Komagateala* (see, e.g. Yurimoto et al., Intern. J. Microbiol. 2011 (2011), ID 101298), of the genus *Sporobolomyces* (e.g. *Sporobolomyces roseus* strain Y) or of the genus *Rhodotorula* (e.g. *Rhodotorula glutinis* strain CY), of the genus *Hansenula* (e.g. *Hansenula polymorpha*)

The genetic modification of microorganisms to express an enzyme of interest will also be further described in detail below.

The phosphoketolase and/or sulfoacetaldehyde acetyltransferase used in the method according to the invention can be a naturally occurring phosphoketolase or sulfoacetaldehyde acetyltransferase or it can be a phosphoketolase/sulfoacetaldehyde acetyltransferase which is derived from a naturally occurring phosphoketolase/sulfoacetaldehyde acetyltransferase, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic modification in prokaryotic cells, a nucleic acid molecule encoding phosphoketolase or a sulfoacetaldehyde acetyltransferase can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting phosphoketolase/sulfoacetaldehyde acetyltransferase variants are then tested for the desired activity, e.g., enzymatic activity, with an assay as described above and in particular for their increased enzyme activity.

As described above, the microorganism employed in a method of the invention or contained in the composition of the invention may be a microorganism which has been genetically modified by the introduction of a nucleic acid molecule encoding a phosphoketolase and/or a sulfoacetaldehyde acetyltransferase. Thus, in a preferred embodiment, the microorganism is a recombinant microorganism which has been genetically modified to have an increased phosphoketolase activity and/or an increased sulfoacetaldehyde acetyltransferase activity. This can be achieved e.g. by transforming the microorganism with a nucleic acid encoding a phosphoketolase and/or a sulfoacetaldehyde acetyltransferase. A detailed description of genetic modification of microorganisms will be given further below. Preferably, the nucleic acid molecule introduced into the microorganism is a nucleic acid molecule which is heterologous with respect to the microorganism, i.e. it does not naturally occur in said microorganism.

In the context of the present invention, an "increased activity" means that the expression and/or the activity of an enzyme, in particular of the phosphoketolase or the sulfoacetaldehyde acetyltransferase, in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme, e.g. a phosphoketolase or a sulfoacetaldehyde acetyltransferase, so that the corresponding expression/activity in the non-modified microorganism is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the phosphoketolase or sulfoacetaldehyde acetyltransferase are known in the art and have already been described above.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme, in particular a phosphoketolase or a sulfoacetaldehyde acetyltransferase, is expressed so as to lead to the production of a polypeptide having any of the activities described above, e.g. phosphoketolase activity or sulfoacetaldehyde acetyltransferase activity. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), lp1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

When the method according to the invention is carried out in vivo by using an organism/microorganism providing the respective enzyme activities, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical process like the method of the present invention is carried out which involves organisms, preferably microorganisms and/or biochemically active substances, i.e., the enzyme(s) described above derived from such organisms or organisms harbouring the above described enzyme(s). In a bioreactor or a fermenter, this process can either be aerobic or anaerobic. These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

The present invention also relates to a composition containing
(a) formaldehyde and a phosphoketolase; or
(b) formaldehyde and a sulfoacetaldehyde acetyltransferase; or
(c) formaldehyde and a phosphoketolase and a sulfoacetaldehyde acetyltransferase; or
(d) formaldehyde and a microorganism expressing a phosphoketolase; or
(e) formaldehyde and a microorganism expressing a sulfoacetaldehyde acetyltransferase; or
(f) formaldehyde and a microorganism expressing a phosphoketolase and a sulfoacetaldehyde acetyltransferase.

The phosphoketolase/sulfoacetaldehyde acetyltransferase can be a phosphoketolase/sulfoacetaldehyde acetyltransferase as defined above in connection with the method according to the invention. The microorganism contained in the composition can be any suitable microorganism which expresses a phosphoketolase and/or a sulfoacetaldehyde acetyltransferase, in particular a microorganism as described herein above in connection with the method according to the invention.

The present invention furthermore relates to the use of a phosphoketolase or of a sulfoacetaldehyde acetyltransferase or of a microorganism expressing a phosphoketolase and/or sulfoacetaldehyde acetyltransferase for the production of acetyl phosphate from formaldehyde. As regards the phosphoketolase/sulfoacetaldehyde acetyltransferase and the microorganism, the same applies as has been set forth above in connection with a method according to the invention.

FIG. 1: FIG. 1A shows a mass spectrum of an enzymatic reaction for the production of acetyl phosphate from formaldehyde using a phosphoketolase from *L. lactis*. FIG. 1B shows a mass spectrum of a control reaction without enzyme.

FIG. 2: shows the intensity of peak of acetate formed from the transformation of formaldehyde by phosphoketolases in the presence of phosphate.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

Example 1: Cloning, Expression and Purification of Phosphoketolases

Gene Synthesis, Cloning and Expression of Recombinant Enzymes

The sequences of phosphoketolases inferred from the genomes of prokaryotic organisms were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The genes thus synthesized were cloned in a modified pUC18 expression vector (New England Biolabs) containing a modified Multiple Cloning Sites (MCS). The genes of interest were cloned at PacI and NotI restriction sites.

Competent MG1655 *E. coli* cells were transformed with these vectors using standard heat shock procedure. The transformed cells were grown in LB-ampicillin medium for 24 h at 30° C., 160 rpm shaking.

The cells were collected by centrifugation at 4° C., 10,000 rpm for 20 min and the pellets were stored at −80° C.

Protein Purification and Concentration

The pellets from 200 ml of cultured cells were thawed on ice and resuspended in 3 ml of 50 mM Tris-HCl pH 7.5 containing 300 mM NaCl, 5 mM $MgCl_2$, 1 mM DTT and 10 mM Imidazole. 10 µl of lysonase (Merck) was added. Cells were incubated 10 minutes at room temperature and then returned to ice for 20 minutes. Cell lysis was completed by sonication for 2×30 seconds. The bacterial extracts were then clarified by centrifugation at 4° C., 10,000 rpm for 20 min. The clarified bacterial lysates were loaded on PRO-TINO-1000 Ni-TED column (Macherey-Nagel) allowing adsorption of 6-His tagged proteins. Columns were washed and the enzymes of interest were eluted with 4 ml of 50 mM Tris-HCl pH 7.5 containing 300 mM NaCl, 5 mM $MgCl_2$, 1 mM DTT, 250 mM Imidazole. Eluates were then concentrated, desalted on Amicon Ultra-4 10 kDa filter unit (Millipore) and enzymes were resuspended in 50 mM Tris-HCl pH 7.5. Enzyme preparation was complemented with 10% glycerol prior to long-term storage. Protein concentrations were quantified by direct UV 280 nm measurement on the NanoDrop 1000 spectrophotometer (Thermo Scientific). The purity of proteins thus purified varied from 70% to 90%.

Example 2: Study of Enzyme-Catalyzed Production of Acetyl Phosphate from Formaldehyde Acetyl phosphate is particularly unstable to hydrolysis, releasing acetate. Therefore, the enzyme-catalyzed production of acetate from formaldehyde was monitored using Mass Spectrometry (MS) and HPLC analysis.

Mass Spectrometry (MS) Analysis

The enzymatic reactions were carried out under the following conditions: 50 mM Sodium phosphate pH 7.5
1 mM Thiamine pyrophosphate (TPP)
10 mM $MgCl_2$
50 mM Formaldehyde (Sigma)
The pH was adjusted to 7.5
Phosphoketolase (PKT) concentration was 10 mg/ml.

Control assays were performed in which either no enzyme was added, or no formaldehyde was added. The enzymatic reactions were run in total volume of 0.2 ml for 40 hours with shaking at 37° C. Typically, an aliquot of 200 µl reaction was removed, centrifuged and the supernatant was transferred into a clean vial. The MS spectra were obtained on Ion Trapp Mass Spectrometer (Esquire 3000, Bruker) in negative ion mode by direct injection of sample using a syringe pump operated at a flow rate of 2 ml/h. The presence of acetate was evaluated. MS analysis showed an $[M-H]^-$ ion at m/z 59.4, corresponding to acetate, from the enzymatic sample but not from the controls (FIGS. 1A and B, FIG. 2).

HPLC-Based Analysis

The enzymatic reactions were carried out under the following conditions:
50 mM Sodium phosphate pH 7.5
5 mM Thiamine pyrophosphate (TPP)
5 mM $MgCl_2$
1.9 mM L-cysteine hydrochloride
23 mM Sodium fluoride
50 mM Formaldehyde (Sigma)
The pH was adjusted to 7.5
Phosphoketolase (PKT) was added at concentration of 5 mg/ml.

Control reactions consisting of (a) formaldehyde and phosphate without enzyme, (b) formaldehyde and enzyme without phosphate were run in parallel.

The enzymatic reactions were run in total volume of 0.3 ml for 48 hours with shaking at 37° C. and stopped by a 5-min incubation at 80° C. The assays tubes were then centrifuged and 100 µl of the clarified supernatant was transferred into a clean vial. Commercial sodium acetate (Sigma-Aldrich) was used as reference. HPLC analyses were performed using a 1260 Infinity LC System (Agilent), equipped with a refractometer detector and a column heating module. 10 µl sample was separated on Hi-Plex H column (300×7.7 mm, 8 µm particle size, column temp. 65° C.) equipped with a PL Hi-Plex H Guard Column (50×7.7 mm). The mobile phase consisted of aqueous sulfuric acid (5.5 mM) was run with a flow rate of 0.6 ml/min. Retention time of acetate under these conditions was 18.4 min.

The results of HPLC analysis are shown in Table 1.

TABLE 1

Formation of acetate from formaldehyde as function of presence of phosphate in reaction mixture.

| | Acetate peak area, arbitrary units | |
|---|---|---|
| Phosphoketolase (PKT) | No phosphate | In the presence of 50 mM sodium phosphate |
| No PKT | | 0 |
| PKT from *Lactococcus lactis* subsp. *lactis* (strain KF147; Uniprot A9QST6; SEQ ID NO: 3) | below the detection limit | 0.26 |
| PKT from *Bifidobacterium pseudolongum* subsp. *globosum* (Uniprot Q6R2Q6; SEQ ID NO: 1) | below the detection limit | 0.23 |
| PKT from *Clostridium acetobutylicum* (strain ATCC 824; Uniprot Q97JE3; SEQ ID NO: 2) | below the detection limit | 0.16 |

These data indicate that production of acetate from formaldehyde takes place in the presence of phosphate and phosphoketolase proceeding through the formation of acetyl phosphate.

Example 3: Study of Production of Acetyl Phosphate from Formaldehyde, Catalyzed by Sulfoacetaldehyde Acetyltransferases Acetyl phosphate is particularly unstable to hydrolysis, releasing acetate. Therefore, the enzyme-catalyzed production of acetate from formaldehyde is monitored using HPLC analysis.

HPLC-Based Analysis

The enzymatic reactions are carried out under the following conditions:
50 mM sodium phosphate pH 7.5
5 mM thiamine pyrophosphate (TPP)
5 mM $MgCl_2$
1.9 mM L-cysteine hydrochloride
23 mM sodium fluoride
50 mM formaldehyde (Sigma-Aldrich)
1-10 mg/ml of enzyme The following enzymes are used in this study:
Sulfoacetaldehyde acetyltransferase from *Alcaligenes xylosoxydans xylosoxydans* (Uniprot Accession number: Q84H41)
Sulfoacetaldehyde acetyltransferase from *Roseovarius nubinhibens* ISM (Uniprot Accession number: A3SR25)
Sulfoacetaldehyde acetyltransferase from *Castellaniella defragans* (Uniprot Accession Number: Q84H44)
Sulfoacetaldehyde acetyltransferase from *Desulfonispora thiosulfatigenes* (Uniprot Accession Number: Q93PS3)

Control reactions consisting of (a) formaldehyde and phosphate without enzyme, (b) formaldehyde and enzyme without phosphate are run in parallel.

The enzymatic reactions are conducted in a total volume of 0.3 ml for 48 hours with shaking at 37° C. and stopped by a 5-min incubation at 80° C. The assays tubes are then centrifuged and 100 µl of the clarified supernatant is transferred into a clean vial. Commercial sodium acetate (Sigma-Aldrich) is used as reference. HPLC analyses are performed using a 1260 Inifinity LC System (Agilent), equipped with a refractometer detector and a column heating module. 10 μl sample is separated on Hi-flex H column (300×7.7 mm, 8 μm particle size, column temp. 65° C.) equipped with a PL Hi-flex H Guard Column (50×7.7 mm). The mobile phase, consisting of aqueous sulfuric acid (5.5 mM) is run with a flow rate of 0.6 ml/min. Retention time of acetate under these conditions is 18.4 min.

The invention claimed is:

1. A method of producing acetyl phosphate, wherein the method comprises:
   (a) contacting formaldehyde and phosphate with a phosphoketolase (EC 4.1.2.9), a fructose-6-phosphate phosphoketolase (EC 4.1.2.22) or a Sulfoacetaldehyde acetyltransferase (EC 2.3.3.15); and
   (b) enzymatically converting formaldehyde and phosphate into acetyl phosphate by the phosphoketolase (EC 4.1.2.9), the fructose-6-phosphate phosphoketolase (EC 4.1.2.22) or the Sulfoacetaldehyde acetyltransferase (EC 2.3.3.15).

2. The method of claim 1, wherein the method further comprises a step of converting the acetyl phosphate into acetate by:
   (a) incubating acetyl phosphate and ADP with an acetate kinase (EC 2.7.2.1) or of a butyrate kinase (EC 2.7.2.7) or of an acetate kinase (diphosphate) (EC 2.7.2.12) or of a propionate kinase (EC 2.7.2.15) to produce acetate and ATP;
   (b) incubating acetyl phosphate and $H_3PO_4$ with an acetate kinase (diphosphate) (EC 2.7.2.12) to produce acetate and diphosphate; or (c) incubating acetyl phosphate and H₂O with an acylphosphatase (EC 3.6.1.7) to produce acetate and H₃PO₄.

3. The method of claim 1, wherein said method further comprises a step of converting the acetyl phosphate into acetyl-coenzyme A by incubating acetyl phosphate and CoA with a phosphate acetyltransferase (EC 2.3.1.8) to produce acetyl-coenzyme A and H₃PO₄.

4. The method of claim 1 further comprising a step of enzymatically converting methanol into formaldehyde by:
   (a) incubating methanol and NAD$^+$ with a methanol dehydrogenase (EC 1.1.1.244) to produce formaldehyde and NADH$^+$ and H$^+$, or
   (b) incubating methanol and two ferricytochrome cL with a methanol dehydrogenase (cytochrome c) (EC 1.1.2.7) to produce formaldehyde, 2 ferrocytochrome cL and 2 H$^+$; or
   (c) incubating methanol and O₂ with an alcohol oxidase (EC 1.1.3.13) to produce formaldehyde and H₂O₂.

5. The method of claim 1, wherein a microorganism expresses the phosphoketolase, the fructose-6-phosphate phosphoketolase and/or the Sulfoacetaldehyde acetyltransferase.

6. The method of claim 4, wherein the formaldehyde is produced by a microorganism.

7. The method of claim 6 wherein the formaldehyde is produced by the microorganism by metabolizing methanol.

8. The method of claim 6, wherein the method further comprises a step of producing acetate and recovering the acetate.

9. The method of claim 7, wherein the method further comprises a step of producing acetate and recovering the acetate.

10. The method of claim 2, wherein the method further comprises a step of recovering the acetate.

11. The method of claim 1, wherein the acetyl phosphate is produced by a microorganism.

12. The method of claim 2, wherein the acetate is produced by a microorganism.

13. The method of claim 3, wherein the acetyl-coenzyme A is produced by a microorganism.

14. The method of claim 7, wherein the microorganism is selected from a methanotrophic bacterium, a methylotrophic bacterium, a methanotrophic yeast or a methylotrophic yeast.

15. The method of claim 11, wherein the formaldehyde is externally provided.

16. The method of claim 2 further comprising a step of enzymatically converting methanol into formaldehyde by:
   (a) incubating methanol and NAD$^+$ with a methanol dehydrogenase (EC 1.1.1.244) to produce formaldehyde and NADH$^+$ and H$^+$; or
   (b) incubating methanol and two ferricytochrome cL with a methanol dehydrogenase (cytochrome c) (EC 1.1.2.7) to produce formaldehyde, 2 ferrocytochrome cL and 2 H$^+$; or
   (c) incubating methanol and O₂ with an alcohol oxidase (EC 1.1.3.13) to produce formaldehyde and H₂O₂.

17. The method of claim 16 wherein the formaldehyde is produced by a microorganism by metabolizing methanol.

18. The method of claim 17, wherein the microorganism is selected from a methanotrophic bacterium, a methylotrophic bacterium, a methanotrophic yeast or a methylotrophic yeast.

19. The method of claim 2, wherein the formaldehyde is externally provided.

20. The method of claim 3 further comprising a step of enzymatically converting methanol into formaldehyde by:
   (a) incubating methanol and NAD$^+$ with a methanol dehydrogenase (EC 1.1.1.244) to produce formaldehyde and NADH$^+$ and H$^+$, or
   (b) incubating methanol and two ferricytochrome cL with a methanol dehydrogenase (cytochrome c) (EC 1.1.2.7) to produce formaldehyde, 2 ferrocytochrome cL and 2 H$^+$; or
   (c) incubating methanol and O₂ with an alcohol oxidase (EC 1.1.3.13) to produce formaldehyde and H₂O₂.

21. The method of claim 20 wherein the formaldehyde is produced by a microorganism by metabolizing methanol.

22. The method of claim 21, wherein the microorganism is selected from a methanotrophic bacterium, a methylotrophic bacterium, a methanotrophic yeast or a methylotrophic yeast.

23. The method of claim 3, wherein the formaldehyde is externally provided.

* * * * *